(12) United States Patent
Huang et al.

(10) Patent No.: US 7,700,304 B2
(45) Date of Patent: Apr. 20, 2010

(54) METHODS OF SCREENING DISORDERS RELATED TO APOE

(75) Inventors: Yadong Huang, San Francisco, CA (US); Robert W. Mahley, San Francisco, CA (US)

(73) Assignee: The J. David Gladstone Institutes, Irvine, CA (US)

( * ) Notice: Subject to any disclaimer, the term of this patent is extended or adjusted under 35 U.S.C. 154(b) by 1148 days.

(21) Appl. No.: 10/820,618

(22) Filed: Apr. 7, 2004

(65) Prior Publication Data

US 2004/0268423 A1 Dec. 30, 2004

Related U.S. Application Data

(63) Continuation of application No. 10/033,526, filed on Nov. 2, 2001, now Pat. No. 6,787,519.

(60) Provisional application No. 60/245,737, filed on Nov. 3, 2000.

(51) Int. Cl.
*G01N 33/53* (2006.01)
(52) U.S. Cl. .......................................... 435/7.2; 800/3
(58) Field of Classification Search ....................... None
See application file for complete search history.

(56) References Cited

U.S. PATENT DOCUMENTS

| | | | |
|---|---|---|---|
| 5,252,463 | A | 10/1993 | Nelson et al. |
| 5,288,707 | A | 2/1994 | Metternich |
| 5,610,297 | A | 3/1997 | Powers .................... 544/168 |
| 6,046,381 | A | 4/2000 | Mucke et al. |
| 6,127,340 | A | 10/2000 | Green et al. |
| 6,281,206 | B1 | 8/2001 | Lu et al. |

FOREIGN PATENT DOCUMENTS

| | | |
|---|---|---|
| JP | 11-049739 | 2/1999 |
| WO | WO 98/01101 | 1/1998 |

OTHER PUBLICATIONS

Tolar et al. (Aug. 15, 1999) Truncated Apolipoprotein E (ApoE) Causes Increased Intracellular Calcium and May Mediate ApoE Neurotoxicity. J Neurosci. 19(16): 7100-7110.
Sigma Chemical Company, Product Detail Antipain hydrochloride Product No. A6191.
Gay et al., "Apolipoprotein E-Derived Peptides Block alpha7 Neuronal Nicotinic Acetylcholine Receptors Expressed in Xenopus Oocytes" Journal of Pharmacology and Experimental Therapeutics, 316(2):835-842 (2006).
Li et al., "Apolipoprotein E-Derived Peptides Ameliorate Clinical Disability and Inflammatory Infiltrates into the Spinal Cord in a Murine of Multiple Sclerosis" Journal of Pharmacology and Experimental Therapeutics, 318(3):956-965 (2006).
Weisgraber et al., "Human apolipoprotein E: the Alzheimer's disease connection" The FASEB Journal, 10:1485-1494 (Nov. 1996).
Weisgraber et al., "ApolipoproteinE: Structure-Function Relationships" Advances in Protein Chemistry, Academic Press, Inc., 45:249-302 (1994).
Lynch, et al. A novel therapeutic derived from apolipoprotein E reduces brain inflammation and improves outcome after closed head injury. Exp Neurol. Mar. 2005;192(1):109-16.
McAdoo, et al. Intrathecal administration of a novel apoE-derived therapeutic peptide improves outcome following perinatal hypoxic-ischemic injury. Neurosci Lett. Jun. 24, 2005;381(3):305-8.
Mahley and Huang (1999) *Curr. Opin. Lipidol.* 10:207-217.
Dallongeville (1992) *J. Lipid Res.* 33:447-454.
Slooter et al. (1997) JAMA 277 :818-821.
Nicoll et al. (1996) *Neuropathol. Appl. Neurobiol.* 22:515-517.
Selkoe (1991) *Neuron* 6:487-498.
Roses, et al. (1994) *Curr. Opinion Biotechnol.* 5:663-667.
Huang et al. (2001) *Proc. Natl. Acad. Sci. USA* 98:8838-8843.
Huang, Y. et al., Apolipoprotein E fragments present in Alzheimer's disease brains induce neurofibrillary tangle-like intracellular inclusions in neurons. PNAS, 2001, vol. 98, No. 15, pp. 8838-8843.
Emilien, G. et al., Alzheimer Disease Mouse Models pabe the way for thrapeutic opportunities. Neurological Review, 2000, vol. 57, pp. 176-181.
Huang, Y. et al., Bioactive fragments of apolipoprotein E induce neurofibrillary tangles in cultured neurons. Society for Neuroscience Abstracts, 2000, vol. 26, No. 1-2, 202.8.
Tolar et al. (Aug. 15, 1999) Truncated Apolipoprotein E (ApoE) Causes Increased Intracellular Calcium and May Mediate ApoE Neurotoxicity. J Neurosci. 19(16): 7100-7110.
Bi et al. (Jul. 17, 2001) "Rapid induction of intraneuronal neurofibrillary tangles in Apolipoprotein E-deficient mice." PNAS 98(15 8832-8837.
Kopito (Dec. 2000) "Aggresomes, inclusion bodies and protein aggregation." Trends Cell Biol. 10(12):524-30.
Ljundberg et al. (May 7, 2002) "Truncated apoE forms tangle-like structures in a neuronal cell line." Molecular Neuroscience 13(6): 867-870.
Patent Abstracts of Japan, vol. 1999, No. 5, May 31, 1991 & JP 11 049739, Nippon Steel Corp, Feb. 23, 1999.

(Continued)

*Primary Examiner*—Michael Pak
(74) *Attorney, Agent, or Firm*—Paula A. Borden; Bozicevic, Field & Francis LLP

(57) ABSTRACT

The present invention provides methods inhibiting formation of neurofibrillary tangles; and methods for treating disorders relating to apolipoprotein E (apoE) in a subject. The methods generally involve reducing the level of a carboxyl-terminal truncated form of apoE in a neuronal cell of a subject. The invention further provides isolated cells comprising a nucleic acid molecule encoding a carboxyl-terminal truncated form of apoE; and methods of screening compounds using the cells. The invention further provides compounds that inhibit an apoE cleavage enzyme, and that reduce the formation of neurofibrillary tangles in a neuronal cell. The invention further provides transgenic non-human animals that include as a transgene a nucleic acid that encodes a carboxyl-terminal truncated form of apoE; as well as methods of screening compounds using transgenic animals.

7 Claims, 8 Drawing Sheets

OTHER PUBLICATIONS

Golabek Adam, et al., "Sodium Dodecyl Sulfate-Resistant Complexes of Alzheimer's Amyloid beta-peptide with the N-Terminal, Receptor Binding Domain of Apolipoprotein E" Biophysical Journal, vol. 79, No. 2, Aug. 2000, pp. 1008-1015.

Marques M. A. et al., "A Thrombin Cleavage Fragment of Apolipoprotein E Exhibits Isoform-Specific Neurotoxicity" Neuroreport, Rapid Communications of Oxford, Oxford GB, vol. 7, No. 15-17, Nov. 4, 1996.

Aleshkov Sergel B. et al., "Contribution of Cyteine 158, the Glycosylation Site Theonine 194, the Amino-and Carboxy-Terminal Domains of Apolipoprotein E in the Biding of Amyloid Peptide Beta (1-40)" Biochemistry, vol. 38, No. 28, Jul. 13, 1999.

Tolar M. et al., "Neurotoxicity of the 11 KDA Thrombin-Cleavage Fragment of Apolipoprotein E and Related Synthetic Peptides is Receptor-Mediated", Journal of Neuroscience, New York, NY, vol. 17, No. 15, pp. 5678-5686, (1997).

Dong L. M. et al., "Human Apolipoprotein E Role of Arginine 61 in Mediating the Lipoprotein Preferences of the E3 and E4 Isoforms", Journal of Biological Chemistry, The American Society of Biological Chemists, Inc., U.S. vol. 269, No. 35, Sep. 2, 1994.

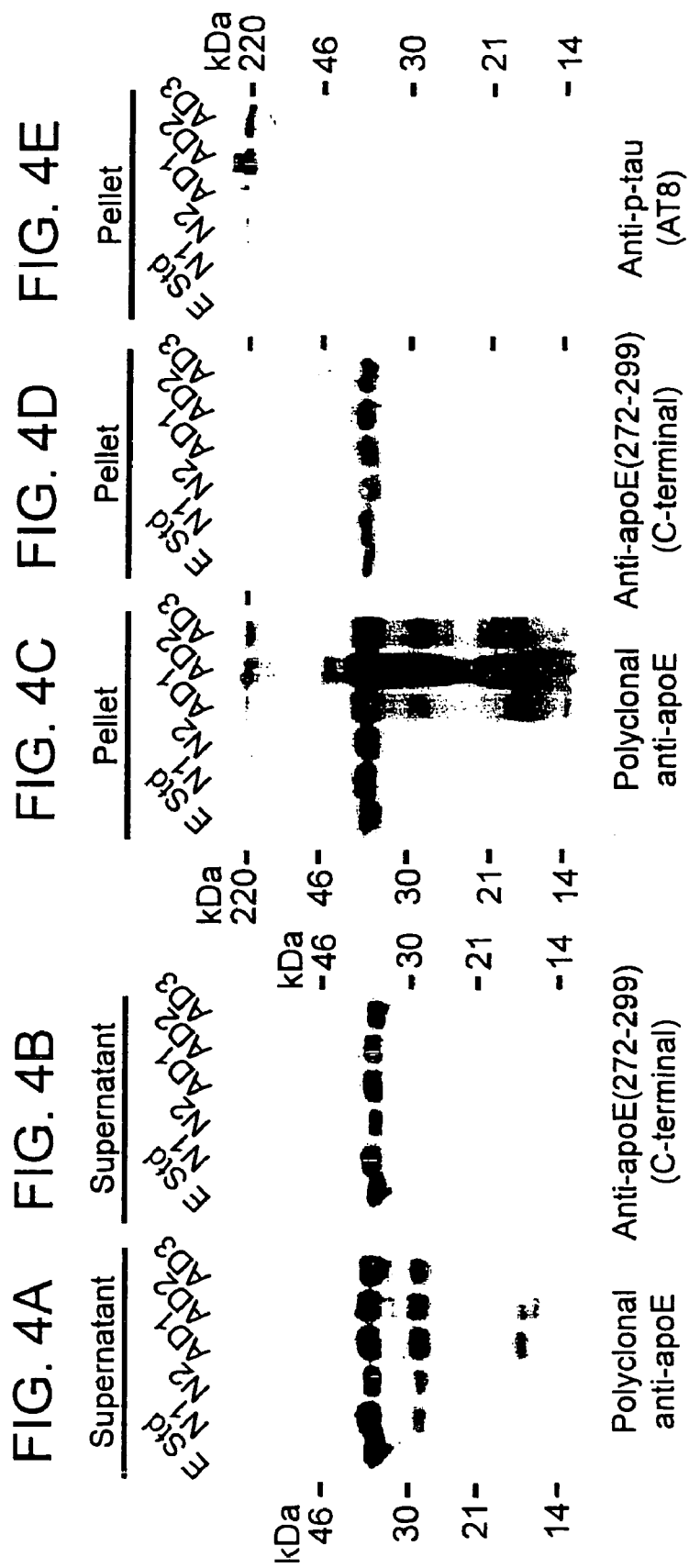

METHODS OF SCREENING DISORDERS RELATED TO APOE

CROSS-REFERENCE

This application claims the benefit of U.S. Provisional Patent Application No. 60/245,737, filed Nov. 3, 2000, which application is incorporated herein by reference in its entirety.

FIELD OF THE INVENTION

The invention relates to apolipoprotein E, and in particular to methods of treating disorders relating to ApoE.

BACKGROUND OF THE INVENTION

Human apolipoprotein (apo) E has three major isoforms, apoE2, apoE3, and apoE4 (for review see Mahley and Huang (1999) *Curr. Opin. Lipidol.* 10:207-217). It has been established that apoE4 is associated with increased plasma cholesterol levels and higher risk for the development of coronary heart disease. Dallongeville (1992) *J. Lipid Res.* 33:447-454. ApoE4 has also been linked to the pathogenesis of Alzheimer's disease. The apoE4 allele is a major risk factor or susceptibility gene associated with approximately 40-65% of cases of sporadic and familial Alzheimer's disease and it increases the occurrence and lowers the age of onset of the disease. Corder et al. (1993) *Science* 261:921-923. In addition, the apoE4 allele is also associated with poor clinical outcome in patients with acute head trauma and stroke. Slooter et al. (1997) JAMA 277:818-821; and Nicoll et al. (1996) *Neuropathol. Appl. Neurobiol.* 22:515-517.

The neuropathological hallmarks of Alzheimer's disease are the presence of neuritic amyloid plaques and neurofibrillary tangles in the brain. Selkoe (1991) *Neuron* 6:487-498; and Roses, et al. (1994) *Curr. Opinion Biotechnol.* 5:663-667. The neuritic plaques represent extracellular deposits of amyloid. The major component of the deposits is the amyloid beta (Aβ) peptide (DS487), which is the proteolytic product of the amyloid precursor protein (APP). In contrast to amyloid plaques, neurofibrillary tangles are primarily intracellular deposits composed largely of highly phosphorylated microtubule-associated protein, tau (p-tau), and, to a lesser extent, phosphorylated NF-H (p-NF-H). ApoE is found in both amyloid plaques and the neurofibrillary tangles There are many hypotheses to explain the association of apoE4 allele with the development of Alzheimer's disease, including its modulation of amyloid β (Aβ) deposition or clearance in the brain, and a lack of interaction of apoE4 with the microtubule-associated protein, tau, which binds to and stabilizes microtubules.

Alzheimer's disease is an insidious and progressive neurological disorder for which there is currently no cure. In view of the lack of adequate treatment for Alzheimer's disease, there exists a need for novel treatment methods for this neurological disorder. The instant invention provides methods of treating disorders relating to ApoE4, and methods of reducing neurofibrillary tangles associated with Alzheimer's disease.

Literature

Huang et al. (2001) *Proc. Natl. Acad. Sci. USA* 98:8838-8843; U.S. Pat. No. 6,046,381.

SUMMARY OF THE INVENTION

The present invention provides methods inhibiting formation of neurofibrillary tangles; and methods for treating disorders relating to apolipoprotein E (apoE) in a subject. The methods generally involve reducing the level of a carboxyl-terminal truncated form of apoE in a neuronal cell of a subject. The invention further provides isolated cells comprising a nucleic acid molecule encoding a carboxyl-terminal truncated form of apoE; and methods of screening compounds using the cells. The invention further provides compounds that inhibit an apoE cleavage enzyme, and that reduce the formation of neurofibrillary tangles in a neuronal cell. The invention further provides transgenic non-human animals that include as a transgene a nucleic acid that encodes a carboxyl-terminal truncated form of apoE; as well as methods of screening compounds using transgenic animals.

BRIEF DESCRIPTION OF THE DRAWINGS

FIG. 4 depicts protein blots of brain lysates from normal individuals (N1 and N2) and individuals with Alzheimer's disease (AD1, AD2, and AD3), immunoprecipitated with anti-apoE antibody.

DETAILED DESCRIPTION OF THE INVENTION

Figure 1:
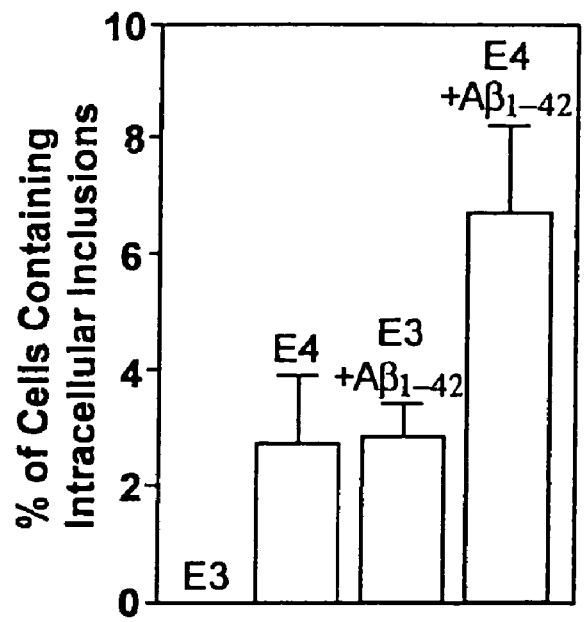
FIG. 1 is a graph depicting the effect of Aβ1-42 on formation of intracellular inclusions in Neuro-2A cells producing apoE.

The present invention is based on the observation that carboxyl-terminal truncated apoE induces formation of neurofibrillary tangle-like structures in cultured neurons. Truncation of up to 30 amino acids from the carboxyl terminus of apoE results in intracellular inclusions in cultured neuronal cells. The inventors found that C-terminal truncated forms of apoE, but not full length apoE, interact with the phosphorylated form of the microtubule associated protein p-tau and the phosphorylated neurofilament protein of high molecular weight, p-NF-H, and induce neurofibrillary tangle (NFT)-like structures in cells. This effect is specific to neuronal cells.

The NFT-like structures induced by C-terminal truncated apoE are similar in many aspects to NFT seen in the brain of Alzheimer's disease (AD) patients. First, the formation of NFT-like structures induced by C-terminal truncated apoE is neuron-specific. Second, the NFT-like structures contain p-tau, which is a major component of NFT in AD brains, and pNF-H, which is also found in NFT in AD brains. Third, electron microscopy reveals that the NFT-like structures induced by truncated apoE are composed of many irregular filaments, with diameters of 10-20 nm, which are similar to some NFT seen in human AD brains.

The present invention provides methods of inhibiting formation of neurofibrillary tangles; and methods for treating disorders relating to apolipoprotein E (apoE) in a subject. The methods generally involve reducing the level of a carboxyl-terminal (C-terminal) truncated form of apoE in a neuronal cell of a subject and/or blocking the interaction of the carboxyl-terminal truncated apoE with p-tau and/or p-NF-H.

The invention further provides isolated cells that include a nucleic acid encoding a C-terminal truncated form of apoE. The subject cells are useful for screening compounds that block the interaction of the carboxyl-terminal truncated apoE with p-tau and/or p-NF-H, and which therefore reduce formation of neurofibrillary tangles.

The invention further provides in vitro screening methods for identifying compounds that reduce the formation of carboxyl-terminal truncated apoE and/or that block the interaction of the carboxyl-terminal truncated apoE with p-tau and/or p-NF-H in a cell. In vitro screening methods for identifying compounds that reduce the formation of carboxyl-terminal truncated apoE involve the use of host cells that produce full-length apoE that is subsequently proteolytically processed to carboxyl-terminal truncated apoE. In vitro screening methods for identifying compounds that block the interaction of the carboxyl-terminal truncated apoE with p-tau and/or p-NF-H generally involve the use of subject host cells that include a nucleic acid encoding a C-terminal truncated form of apoE. Compounds identified using an in vitro screening assay of the invention are candidate compounds for treating disorders arising from the presence in a neuronal cell of C-terminal truncated forms of apoE, including AD.

The invention further provides transgenic non-human animals that include as a transgene a nucleic acid that encodes a carboxyl-terminal truncated form of ApoE. The subject non-human transgenic animals are useful for screening compounds that block the interaction of the carboxyl-terminal truncated apoE with p-tau and/or p-NF-H.

The invention further provides in vivo screening methods for identifying compounds that reduce the formation of carboxyl-terminal truncated apoE and/or that block the interaction of the carboxyl-terminal truncated apoE with p-tau and/or p-NF-H in a cell. In vivo screening methods for identifying compounds that reduce the formation of carboxyl-terminal truncated apoE involve the use of transgenic non-human animals that include as a transgene a nucleic acid that encodes full-length apoE, and that produce, in neuronal cells, full-length apoE that is subsequently proteolytically processed to carboxyl-terminal truncated apoE. In vivo screening methods for identifying compounds that block the interaction of the carboxyl-terminal truncated apoE with p-tau and/or p-NF-H generally involve the use of subject transgenic non-human animals that include as a transgene a nucleic acid that encodes a carboxyl-terminal truncated form of apoE, and that produce, in neuronal cells, a carboxyl-terminal truncated apoE. Compounds identified using an in vivo screening assay of the invention are candidate compounds for treating disorders arising from the presence in a neuronal cell of C-terminal truncated forms of apoE, including AD.

The invention further provides compounds that inhibit an apoE cleavage enzyme, and compositions, e.g., pharmaceutical compositions, that include the compounds. The compounds are useful for reducing the level of neurofibrillary tangles in a neuronal cell, and thus are useful for treating disorders such as AD.

DEFINITIONS

As used herein, the terms "a disorder associated with apoE," "a disorder related to carboxyl-terminal truncated apoE" and "a disease associated with carboxyl-terminal truncated apoE" are used interchangeably to refer to any disease or disorder which is associated with the presence in an individual of carboxyl-terminal truncated apoE. A disease or disorder related to carboxyl-terminal truncated apoE may be a direct or indirect result of the presence of carboxyl-terminal truncated apoE in the individual. For example, a disease or disorder related to carboxyl-terminal truncated apoE is one that occurs as a result of the formation of neurofibrillary tangles in a neuronal cell. A disease or disorder related to carboxyl-terminal truncated apoE may also be a disease or disorder for which carboxyl-terminal truncated apoE is a risk factor, e.g., the presence in an individual of carboxyl-terminal truncated apoE increases the individual's risk of developing the disease or disorder. Diseases and disorders associated with carboxyl-terminal truncated apoE include, but are not limited to sporadic Alzheimer's disease; familial Alzheimer's disease; diseases associated with increased plasma levels of cholesterol, such as coronary artery disease; and poor clinical outcome in patients with acute head trauma; and poor clinical outcome in patients with stroke.

The term "Alzheimer's disease" (abbreviated herein as "AD") as used herein refers to a condition associated with formation of neuritic plaques comprising amyloid β protein primarily in the hippocampus and cerebral cortex, as well as impairment in both learning and memory. "AD" as used herein is meant to encompass both AD as well as AD-type pathologies.

The term "phenomenon associated with Alzheimer's disease" as used herein refers to a structural, molecular, or functional event associated with AD, particularly such an event that is readily assessable in an animal model. Such events include, but are not limited to, amyloid deposition, neuropathological developments, learning and memory deficits, and other AD-associated characteristics.

As used herein, the terms "determining," "measuring," and "assessing," and "assaying" are used interchangeably and include both quantitative and qualitative determinations.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents, solubilization, or enrichment for certain components, such as polynucleotides. The term "biological sample" encompasses a clinical sample, and also includes cells in culture, cell supernatants, cell lysates, serum, plasma, biological fluid, and tissue samples.

The terms "polynucleotide" and "nucleic acid molecule" are used interchangeably herein to refer to polymeric forms of nucleotides of any length. The polynucleotides may contain deoxyribonucleotides, ribonucleotides, and/or their analogs. Nucleotides may have any three-dimensional structure, and may perform any function, known or unknown. The term "polynucleotide" includes single-, double-stranded and triple helical molecules. "Oligonucleotide" generally refers to polynucleotides of between about 5 and about 100 nucleotides of single- or double-stranded DNA. However, for the purposes of this disclosure, there is no upper limit to the length of an oligonucleotide. Oligonucleotides are also known as oligomers or oligos and may be isolated from genes, or chemically synthesized by methods known in the art.

The terms "polypeptide" and "protein", used interchangeably herein, refer to a polymeric form of amino acids of any length, which can include coded and non-coded amino acids, chemically or biochemically modified or derivatized amino acids, and polypeptides having modified peptide backbones. The term includes fusion proteins, including, but not limited to, fusion proteins with a heterologous amino acid sequence, fusions with heterologous and homologous leader sequences, with or without N-terminal methionine residues; immunologically tagged proteins; fusion proteins with detectable fusion partners, e.g., fusion proteins including as a fusion partner a fluorescent protein, β-galactosidase, luciferase, etc.; and the like.

As used herein the term "isolated" is meant to describe a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, preferably 75% free, and most preferably 90% free from other components with which it is naturally associated.

The term "transgene" is used herein to describe genetic material that has been or is about to be artificially inserted into the genome of a cell, particularly a mammalian cell for implantation into a living animal. The transgene is used to transform a cell, meaning that a permanent or transient genetic change, preferably a permanent genetic change, is induced in a cell following incorporation of exogenous DNA. A permanent genetic change is generally achieved by introduction of the DNA into the genome of the cell. Vectors for stable integration include plasmids, retroviruses and other animal viruses, YACs, and the like. Of interest are transgenic mammals, e.g. cows, pigs, goats, horses, etc., and particularly rodents, e.g. rats, mice, etc.

The terms "treatment" "treating" and the like are used herein to encompass any treatment of any disease or condition in a mammal, particularly a human, and includes: a) preventing a disease, condition, or symptom of a disease or condition from occurring in a subject which may be predisposed to the disease but has not yet been diagnosed as having it; b) inhibiting a disease, condition, or symptom of a disease or condition, e.g., arresting its development and/or delaying its onset or manifestation in the patient; and/or c) relieving a disease, condition, or symptom of a disease or condition, e.g., causing regression of the condition or disease and/or its symptoms.

The terms "subject," "host," "patient," and "individual" are used interchangeably herein to refer to any mammalian subject for whom diagnosis or therapy is desired, particularly humans. Other subjects may include cattle, dogs, cats, guinea pigs, rabbits, rats, mice, horses, and so on.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a carboxyl-terminal truncated apoE protein" includes a plurality of such proteins and reference to "the cell" includes reference to one or more cells and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

ApoE Polypeptide Fragments

The present invention provides isolated apoE polypeptide fragments, and compositions including such polypeptide fragments. ApoE polypeptide fragments include carboxyl-terminal truncated apoE; and fragments that include at least amino acids 244-260 of apoE. Carboxyl-truncated apoE polypeptides are useful in screening assays to identify agents that reduce formation of neurofibrillary tangles, as described below. Fragments that include at least amino acids 244-260 of apoE are useful to inhibit apoE binding to p-tau and p-NF-H, thereby reducing formation of neurofibrillary tangles.

Carboxyl-terminal truncations of apoE include any carboxyl-terminal truncated form of apoE that binds both p-tau and p-NF-H and induces formation of neurofibrillary tangles that include carboxyl-terminal truncated apoE, p-tau, and p-NF-H in a neuronal cell. Whether a given carboxyl-terminal truncated apoE polypeptide binds p-tau, binds p-NF-H, and forms neurofibrillary tangles in a neuronal cell is readily determined by those skilled in the art using known assays. For example, formation of complexes that include carboxyl-terminal truncated apoE polypeptide, p-tau, and p-NF-H can be detected using antibodies specific for each of these proteins, using, e.g., established techniques of cell staining; established techniques for co-immunoprecipitation; protein ("Western") blotting; and the like, e.g., as described in the Examples. Formation of neurofibrillary tangles can be assessed visually, e.g., by observing intracellular inclusions in neuronal cells. Whether such neurofibrillary tangles include carboxyl-terminal truncated apoE, p-tau, and p-NF-H can be determined using antibodies specific for each protein.

Deletion of from about 28 to about 30, from about 30 to about 35, from about 35 to about 40, from about 40 to about 45, or from about 45 to about 48 amino acids from the carboxyl terminus of apoE3 or apoE4 results in carboxyl-terminal truncated apoE that bind p-tau, bind p-NF-H, and induce formation of neurofibrillary tangles in a neuronal cell. Specific carboxyl-terminal truncated apoE polypeptides that give rise to neurofibrillary tangles include, but are not limited to, apoE4Δ272-299; apoE3Δ272-299; apoE4Δ261-299; and apoE4Δ252-299.

The invention further provides fragments of apoE that correspond to the portion of apoE that interacts with p-tau and p-NF-H. Such fragments include at least amino acids 244-260 of the apoE polypeptide (apoE244-260). Also included are apoE244-260 fragments that include additional carboxyl- and/or amino-terminus additions of from 1 to about 5, from about 5 to about 10, from about 10 to about 15, or from about 15 to about 20 amino acids. Such fragments are useful to inhibit binding of apoE with p-tau and p-NF-H.

Nucleic Acids and Host Cells

The present invention provides nucleic acids that include a nucleotide sequence that encodes a carboxyl-terminal truncated apoE polypeptide, as well as host cells that contain the nucleic acid. In some embodiments, the host cells are isolated. In other embodiments, the host cells are part of a transgenic, non-human animal that includes, as a transgene, a nucleic acid of the invention.

Nucleic Acids

The subject nucleic acid molecules may be part of a vector ("construct") for use in generating a transgenic, non-human animal of the invention, as described below, or for use in generating a recombinant host cell that produces a carboxyl-terminal truncated apoE polypeptide. In addition, a nucleic acid molecule of the invention may encode all or part of a carboxyl-terminal truncated apoE polypeptide of the invention, and as such is useful, as part of an expression vector, in producing carboxyl-terminal truncated apoE polypeptide.

The sequence of the mouse apoE gene is found under Genbank accession number D00466. Various primate apoE gene sequences are found under GenBank accession numbers AF200508, AF200507, AF200506, and AH009953 (*Hylobates lar*, or gibbon); AH009952, AF200503, AF200504, and AF200505 (*Pongo pygmaeus*, or orangutan); AH009951, AF200500, AG200501, and AF200502 (*Gorilla gorilla*); AH009950, AF200497, AF200498, AF200499 (*Pan troglodytes*, or chimpanzee). Any apoE-encoding sequence can be modified to encode a carboxyl-terminal truncated apoE polypeptide as described above.

In some embodiments, nucleic acids of the invention include the open reading frame encoding carboxyl-terminal truncated apoE polypeptide, one or more introns, may further include adjacent 5' and 3' non-coding nucleotide sequences involved in the regulation of expression, and are generally up to about 10 kb in total length, but possibly longer. The DNA sequences encoding all or part of the recombinant apoE are genomic DNA or a fragment thereof. The apoE gene encoding carboxyl-terminal truncated apoE may be introduced into an appropriate vector for extrachromosomal maintenance or for integration into the host.

A genomic sequence of interest comprises the nucleic acid present between the initiation codon and the stop codon, except for those nucleotides encoding carboxyl-terminal amino acids, as discussed above, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' or 3' end of the transcribed region. The genomic DNA may be isolated as a fragment of 100 kbp or smaller; and substantially free of flanking chromosomal sequence.

The sequence of this 5' region, and further 5' upstream sequences and 3' downstream sequences, may be utilized for promoter elements, including enhancer binding sites, that provide for expression in tissues where apoE is expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease. Alternatively, mutations may be introduced into the promoter region to determine the effect of altering expression in experimentally defined systems. Methods for the identification of specific DNA motifs involved in the binding of transcriptional factors are known in the art, e.g. sequence similarity to known binding motifs, gel retardation studies, etc. For examples, see Blackwell et al *Mol Med* 1:194-205 (1995); Mortlock et al. *Genome Res.* 6:327-33 (1996); and Joulin and Richard-Foy *Eur J Biochem* 232:620-626 (1995).

The regulatory sequences may be used to identify cis acting sequences required for transcriptional or translational regulation of apoE expression, especially in different tissues or stages of development, and to identify cis acting sequences and trans acting factors that regulate or mediate expression. Such transcription or translational control regions may be operably linked to carboxyl-terminal truncated apoE polypeptide-encoding apoE gene in order to promote expression of carboxyl-terminal truncated apoE or other proteins of interest in cultured cells, or in embryonic, fetal or adult tissues, and for gene therapy.

In some embodiments, regulatory elements include regulatory elements that result in neuronal cell-specific expression of the operably linked carboxyl-terminal truncated apoE-encoding nucleic acid. Neuronal cell-specific regulatory elements (including promoters, enhancers, and the like) are known to those skilled in the art. Examples of neuronal cell-specific regulatory elements include those from a neuron-specific enolase (NSE) gene (Hannas-Djebarra et al. (1997) *Brain Res. Mol. Brain Res.* 46:91-99); a PDGF gene; a Th1 gene (e.g., mouse Thy1.2 (Caroni et al. (1997) *J. Neurosci. Methods* 71:3-9); a neurofilament gene (e.g., NF-L, NF-M, and NF-L); a glial filament acidic protein gene; a myelin basic protein gene; a microtubule associated protein genes; a synaptophysin gene; a tyrosine hydroxylase gene; and the like.

In other embodiments, a nucleic acid molecule of the invention comprises a cDNA comprising sequences that encode a carboxyl-terminal truncated apoE protein of the invention. The nucleic acid compositions used in the subject invention may encode all or a part of the carboxyl-terminal truncated apoE polypeptides as appropriate. Fragments may be obtained of the DNA sequence by chemically synthesizing oligonucleotides in accordance with conventional methods, by restriction enzyme digestion, by PCR amplification, etc. For the most part, DNA fragments will be of at least 15 nucleotides (nt), usually at least 18 nt, more usually at least about 50 nt. Such small DNA fragments are useful as primers for PCR, hybridization screening, etc. Larger DNA fragments, i.e. greater than 100 nt are useful for production of the encoded polypeptide. For use in amplification reactions, such as PCR, a pair of primers will be used.

In some embodiments, a nucleic acid molecule of the invention comprises nucleotide sequences of a genomic apoE gene, modified as described above such that the encoded apoE protein is a carboxyl-terminal truncated apoE polypeptide. In other embodiments, a nucleic acid molecule of the invention comprises the coding regions of a apoE gene, modified as described above such that the encoded apoE protein is a carboxyl-terminal truncated apoE polypeptide (e.g., a cDNA molecule encoding a carboxyl-terminal truncated apoE).

The invention further provides nucleic acid molecules that comprise a nucleotide sequence that encodes a carboxyl-terminal truncated apoE protein that binds p-tau, binds p-NF-H, and induces formation of neurofibrillary tangles in a neuronal cell, wherein the nucleic acid molecules hybridize under stringent hybridization conditions to one of a mouse genomic apoE gene, modified such that the encoded apoE protein is a carboxyl-terminal truncated apoE; and the coding region of a mouse apoE gene, modified as described above such that the encoded apoE protein is a carboxyl-terminal truncated apoE. Examples of stringent conditions are hybridization and washing at 50° C. or higher and in 0.1×SSC (9 mM NaCl/0.9 mM sodium citrate).

The invention further provides nucleic acid molecules that comprise a nucleotide sequence that encodes a carboxyl-terminal truncated apoE protein that binds p-tau, binds p-NF-H, and induces formation of neurofibrillary tangles in a neuronal cell, wherein the nucleic acid molecules have at least about 75%, at least about 80%, at least about 85%, at least about 90%, at least about 95%, or higher, nucleotide sequence identity with one of a mouse genomic apoE gene, modified such that the encoded apoE protein is a carboxyl-terminal truncated apoE; and the coding region of a mouse apoE gene, modified as described above such that the encoded apoE protein is a carboxyl-terminal truncated apoE polypeptide.

Subject nucleic acid molecules may comprise other, non-apoE nucleic acid molecules ("heterologous nucleic acid molecules") of any length. For example, the subject nucleic acid molecules may be flanked on the 5' and/or 3' ends by heterologous nucleic acid molecules of from about 1 nt to about 10 nt, from about 10 nt to about 20 nt, from about 20 nt to about 50 nt, from about 50 nt to about 100 nt, from about 100 nt to about 250 nt, from about 250 nt to about 500 nt, or from about 500 nt to about 1000 nt, or more in length. For example, when used as a probe to detect nucleic acid molecules capable of hybridizing with the subject nucleic acids, the subject nucleic acid molecules may be flanked by heterologous sequences of any length. Heterologous sequence include, but are not limited to, sequences encoding a reporter protein, and the like.

The subject nucleic acid molecules may also be provided as part of a vector, a wide variety of which are known in the art and need not be elaborated upon herein. Vectors include, but are not limited to, plasmids; cosmids; viral vectors; artificial chromosomes (YAC's, BAC's, etc.); mini-chromosomes; and the like. Vectors are amply described in numerous publications well known to those in the art, including, e.g., Short Protocols in Molecular Biology, (1999) F. Ausubel, et al., eds., Wiley & Sons. Vectors may provide for expression of the subject nucleic acids, may provide for propagating the subject nucleic acids, or both.

The subject nucleic acid molecules are isolated and obtained in substantial purity, generally as other than an intact chromosome. Usually, the DNA will be obtained substantially free of other nucleic acid sequences that do not include a sequence or fragment thereof of the subject genes, generally being at least about 50%, usually at least about 90% pure and are typically "recombinant", i.e. flanked by one or more nucleotides with which it is not normally associated on a naturally occurring chromosome.

The subject nucleic acid compositions find use in the preparation of all or a portion of the carboxyl-terminal truncated apoE polypeptides of the invention, as described above. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to a gene encoding the subject peptides, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme or other protein marker, e.g. β-galactosidase, green fluorescent protein, luciferase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, or any of the above-described fragment, and up to the complete open reading frame of the gene. After introduction of the DNA, the cells containing the construct may be selected by means of a selectable marker, the cells expanded and then used for expression.

Proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, Neuro-2A cells, may be used as the expression host cells. In some situations, it is desirable to express the gene in eukaryotic cells, where the encoded protein will benefit from native folding and post-translational modifications. Small peptides can also be synthesized in the laboratory. Polypeptides that are subsets of the complete sequences of the subject proteins may be used to identify and investigate parts of the protein important for function.

Specific expression systems of interest include bacterial, yeast, insect cell and mammalian cell derived expression systems. A wide variety of such systems are known to those skilled in the art.

Host Cells

Recombinant host cells comprising a subject nucleic acid molecule may serve as a source of carboxyl-terminal truncated apoE protein of the invention. They may also serve in drug screening assays to identify agents that reduce binding of carboxyl-terminal truncated apoE4 to p-tau and p-NF-H in a neuronal cell.

In some embodiments, of particular interest are mammalian cells that normally produce apoE, and cells that normally take up apoE from their environment. Examples of such cells include neuronal cells, microglial cells, and astrocytes. Immortalized neuronal cells, microglial cells, and astrocytes are also of interest.

Transgenic, Non-Human Animals

The present invention provides transgenic, non-human animals, particularly transgenic, non-human mammals that include, as a transgene, an exogenous nucleic acid that includes a coding region for a carboxyl-terminal truncated apoE polypeptide. The transgenic, non-human animals of the invention are useful for screening agents that reduce binding of carboxyl-terminal truncated apoE4 to p-tau and p-NF-H in a neuronal cell, and which therefore reduce the formation of neurofibrillary tangles. Such compounds are candidate agents useful for treating Alzheimer's disease and associated pathologies.

In many embodiments, the carboxyl-terminal truncated apoE-encoding transgene includes neuronal cell-specific regulatory elements such that the carboxyl-terminal truncated apoE is produced primarily in neuronal cells. However, the carboxyl-terminal truncated apoE-encoding transgene does not necessarily include neuronal cell-specific regulatory elements, as neurofibrillary tangles will form only in those cells that produce p-tau and p-NF-H, i.e., neuronal cells.

Methods of generating transgenic, non-human animals, particularly transgenic, non-human mammals, are known in the art. See, e.g., U.S. Pat. Nos. 6,268,545; 6,255,554; 6,222,094; and 6,204,43; "Transgenic Animal Technology" C. A. Pinkert, ed. (1997) Acad. Press; "Gene Knockout Protocols" M. J. Tymms, et al., eds. (2001) Humana Press; and "Gene Targeting: A Practical Approach" A. L. Joyner, ed. (2000) Oxford Univ. Press.

Transgenic animals comprise an exogenous nucleic acid sequence present as an extrachromosomal element or stably integrated in all or a portion of its cells, especially in germ cells. Unless otherwise indicated, it will be assumed that a transgenic animal comprises stable changes to the germline sequence. During the initial construction of the animal, "chimeras" or "chimeric animals" are generated, in which only a subset of cells have the altered genome. Chimeras are primarily used for breeding purposes in order to generate the desired transgenic animal. Animals having a heterozygous alteration are generated by breeding of chimeras. Male and female heterozygotes are typically bred to generate homozygous animals.

In some embodiments, the endogenous apoE gene is knocked out (e.g., rendered non-functional). In the present invention, transgenic knockouts have a partial or complete loss of function in one or both alleles of the endogenous apoE gene.

Where the transgenic animal is a knock-out, the target gene expression is undetectable or insignificant. A knock-out of an endogenous apoE gene means that function of the endogenous apoE protein has been substantially decreased so that expression is not detectable or only present at insignificant levels. This may be achieved by a variety of mechanisms, including introduction of a disruption of the coding sequence, e.g. insertion of one or more stop codons, insertion of a DNA fragment, etc., deletion of coding sequence, substitution of stop codons for coding sequence, etc. In some cases the exogenous transgene sequences are ultimately deleted from the genome, leaving a net change to the native sequence. Different approaches may be used to achieve the "knock-out." See U.S. Pat. Nos. 5,464,764, 5,627,059 and related patents and publications to Capecchi et al. A chromosomal deletion of all or part of the native gene may be induced, including deletions of the non-coding regions, particularly the promoter region, 3' regulatory sequences, enhancers, or deletions of gene that activate expression of apoE genes.

A functional knock-out may also be achieved by the introduction of an anti-sense construct that blocks expression of the native genes (for example, see Li and Cohen *Cell* 85:319-329 (1996)). "Knock-outs" also include conditional knock-outs, for example where alteration of the target gene occurs upon exposure of the animal to a substance that promotes target gene alteration, introduction of an enzyme that promotes recombination at the target gene site (e.g. Cre in the Cre-lox system), or other method for directing the target gene alteration postnatally.

The apoE gene transgene encodes carboxyl-terminal truncated apoE and is a genetically manipulated sequence as discussed above, including deletions in the coding region such that the encoded protein is a carboxyl-terminal truncated apoE protein. The introduced sequence encodes a carboxyl-terminal truncated apoE polypeptide, and may further include additional coding sequences, including, e.g., nucleotides encoding a reporter protein (e.g., β-galactosidase, luciferase, green fluorescent protein, and the like). The transgene includes a carboxyl-terminal truncated apoE-encoding nucleotide sequence operably linked to a promoter, which may be constitutive or inducible, and other regulatory sequences required for expression in the host animal. By "operably linked" is meant that a DNA sequence and a regulatory sequence(s) are connected in such a way as to permit gene expression when the appropriate molecules, e.g. transcriptional activator proteins, are bound to the regulatory sequence(s).

DNA constructs for homologous recombination will comprise a nucleotide sequence encoding carboxyl-terminal truncated apoE, and will include regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. *Methods in Enzymology* 185:527-537 (1990).

For embryonic stem (ES) cells, an ES cell line may be employed, or embryonic cells may be obtained freshly from a host, e.g. mouse, rat, guinea pig, etc. Such cells are grown on an appropriate fibroblast-feeder layer or grown in the presence of appropriate growth factors, such as leukemia inhibiting factor (LIF). When ES cells have been transformed, they may be used to produce transgenic animals. See U.S. Pat. Nos. 5,387,742, 4,736,866 and 5,565,186 for methods of making transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting litters screened for mutant cells having the construct. By providing for a different phenotype of the blastocyst and the ES cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allergenic or congenic grafts or transplants, or in in vitro culture.

Compositions

The present invention further provides compositions, including pharmaceutical compositions, comprising the agents, polypeptides, polynucleotides, recombinant vectors, and host cells of the invention. These compositions may include a buffer, which is selected according to the desired use of the agent, polypeptide, polynucleotide, recombinant vector, or host cell, and may also include other substances appropriate to the intended use. Those skilled in the art can readily select an appropriate buffer, a wide variety of which are known in the art, suitable for an intended use. In some instances, the composition can comprise a pharmaceutically acceptable excipient, a variety of which are known in the art and need not be discussed in detail herein. Pharmaceutically acceptable excipients have been amply described in a variety of publications, including, for example, A. Gennaro (1995) "Remington: The Science and Practice of Pharmacy", 19th edition, Lippincott, Williams, & Wilkins.

Screening Assays

The present invention provides methods for identifying a compound that reduce the formation neurofibrillary tangles in a neuronal cell. Agents that reduce the level of neurofibrillary tangles in a cell include those that reduce proteolytic cleavage of apoE; and those that reduce interaction of carboxyl-terminal truncated apoE with p-tau and p-NF-H. Test agents that have an effect in an assay method of the invention are candidates for treating disorders related to carboxyl-terminal truncated apoE.

In some embodiments, the assays are in vitro cell-based screening methods for identifying compounds that reduce the formation of carboxyl-terminal truncated apoE and/or that block the interaction of the carboxyl-terminal truncated apoE with p-tau and/or p-NF-H in a cell.

In some embodiments, in vitro cell-based screening methods for identifying compounds that reduce the formation of carboxyl-terminal truncated apoE involve the use of host cells that produce full-length apoE that is subsequently proteolytically processed to carboxyl-terminal truncated apoE. The methods generally involve contacting a cell that includes a carboxyl-truncated form of apoE in its cytosol with a candidate agent, and determining the effect of the candidate agent on the level of carboxyl-truncated form of apoE and/or the level of neurofibrillary tangles in the cell, compared to a control. A suitable control lacks the test agent.

In other embodiments, in vitro cell-based screening methods for identifying compounds that block the interaction of the carboxyl-terminal truncated apoE with p-tau and/or p-NF-H generally involve the use of subject host cells that include a nucleic acid encoding a C-terminal truncated form of apoE. The methods generally involve contacting a cell that includes a carboxyl-truncated form of apoE in its cytosol with a candidate agent, and determining the effect of the agent on binding of apoE with p-tau and p-NF-H and/or the level of neurofibrillary tangles in the cell, compared to a control. A suitable control lacks the test agent.

In other embodiments, a screening assay of the invention is an in vitro cell-free method. In vitro cell-free screening methods generally involve contacting an enzyme that mediates proteolytic cleavage of apoE with (1) a substrate for the enzyme, the substrate providing for a detectable signal when the enzyme is active; and (2) a test agent. A control sample includes the enzyme and the substrate, but no test agent. The enzyme may be, but need not be, purified. The enzyme may be in a lysate of a cell that produces carboxyl-terminal truncated apoE; may be partially isolated; or may be substantially isolated (e.g., about 90%, about 95%, or about 98% pure).

Compounds identified using an in vitro screening assay of the invention are candidate compounds for treating disorders arising from the presence in a neuronal cell of C-terminal truncated forms of apoE, including AD.

In other embodiments, screening assays are in vivo screening assays. In some embodiments, in vivo screening methods for identifying compounds that reduce the formation of carboxyl-terminal truncated apoE involve the use of transgenic non-human animals that include as a transgene a nucleic acid that encodes full-length apoE, and that produce, in neuronal cells, full-length apoE that is subsequently proteolytically processed to carboxyl-terminal truncated apoE. In other embodiments, in vivo screening methods for identifying compounds that block the interaction of the carboxyl-terminal truncated apoE with p-tau and/or p-NF-H generally involve the use of subject transgenic non-human animals that include as a transgene a nucleic acid that encodes a carboxyl-terminal truncated form of ApoE, and that produce, in neuronal cells, a carboxyl-terminal truncated apoE.

The methods generally involve contacting the transgenic, non-human animal with a test agent and determining the effect, if any, of a test agent on the level of carboxyl-terminal truncated apoE and/or the level of neurofibrillary tangles in a neuronal cell of the animal, compared to a control. A suitable control includes the transgenic animal not contacted with the test agent. Compounds identified using an in vivo screening assay of the invention are candidate compounds for treating disorders arising from the presence in a neuronal cell of C-terminal truncated forms of apoE, including AD.

Candidate agents (also referred to herein as "test agents") encompass numerous chemical classes, although typically they are organic molecules, e.g., small organic compounds having a molecular weight of more than 50 and less than about 2,500 daltons. Candidate agents generally comprise functional groups necessary for structural interaction with proteins, e.g., van der Waals interactions and hydrogen bonding, and may include at least an amine, carbonyl, hydroxyl or carboxyl group, and may include at least two of the functional chemical groups. The candidate agents often comprise cyclical carbon or heterocyclic structures and/or aromatic or polyaromatic structures substituted with one or more of the above functional groups. Candidate agents are also found among biomolecules including, but not limited to: peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs. New potential therapeutic agents may also be created using methods such as rational drug design or computer modeling.

Screening may be directed to known pharmacologically active compounds and chemical analogs thereof, or to new agents with unknown properties such as those created through rational drug design. Efficacious candidates can be identified by phenotype, i.e. an arrest or reversal of particular cognitive behaviors in comparison with wild-type animals and a transgenic non-human animal of the invention.

Agents that have an effect in an assay method of the invention may be further tested for cytotoxicity, bioavailability, and the like, using well known assays. Agents that have an effect in an assay method of the invention may be subjected to directed or random and/or directed chemical modifications, such as acylation, alkylation, esterification, amidification, etc. to produce structural analogs. Such structural analogs include those that increase bioavailability, and/or reduced cytotoxicity. Those skilled in the art can readily envision and generate a wide variety of structural analogs, and test them for desired properties such as increased bioavailability and/or reduced cytotoxicity and/or ability to cross the blood-brain barriers.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used. The mixture of components is added in any order that provides for the requisite binding. Incubations are performed at any suitable temperature, typically between 4 and 40° C. Incubation periods are selected for optimum activity, but may also be optimized to facilitate rapid high-throughput screening. Typically between 0.1 and 1 hours will be sufficient.

In Vitro Cell-Based Screening Assays

In some embodiments, the invention provides methods for identifying a compound that reduces the formation of neurofibrillary tangles in a cell, generally involving contacting a cell in vitro with a test agent, and determining the effect, if any, of the test agent on the formation of neurofibrillary tangles in the cell. In some embodiments, the methods provide for detecting the presence and/or amount of carboxyl-terminal truncated apoE in the cells, where a reduction in the amount of carboxyl-terminal truncated apoE generally results in a reduction in the amount of neurofibrillary tangles. A test agent that reduces the amount of carboxyl-terminal truncated apoE is generally one that reduces the formation of neurofibrillary tangles in the cell.

In some embodiments, in vitro cell-based screening methods for identifying compounds that reduce the formation of carboxyl-terminal truncated apoE involve the use of host cells that produce full-length apoE that is subsequently proteolytically processed to carboxyl-terminal truncated apoE. Such host cells are generated by introducing into a suitable cell a nucleic acid that encodes full-length apoE. The methods generally involve contacting a cell that produces full-length apoE in its cytosol with a candidate agent, and determining the effect of the candidate agent on the level of carboxyl-truncated form of apoE and/or the level of neurofibrillary tangles in the cell, compared to a control. A suitable control lacks the test agent.

In other embodiments, in vitro cell-based screening methods for identifying compounds that block the interaction of the carboxyl-terminal truncated apoE with p-tau and/or p-NF-H generally involve the use of subject host cells that include a nucleic acid encoding a C-terminal truncated form of apoE. Suitable cells include a subject host cell that includes a carboxyl-terminal truncated apoE-encoding nucleic acid. The methods generally involve contacting a cell that includes a carboxyl-truncated form of apoE in its cytosol with a candidate agent, and determining the effect of the agent on binding of apoE with p-tau and p-NF-H and/or the level of neurofibrillary tangles in the cell, compared to a control. A suitable control lacks the test agent.

The cell used in the screening method is one that includes carboxyl-terminal truncated apoE in the cytosol, and also produces p-tau and p-NF-H. In general, the cell is a neuronal cell, and in many embodiments, the cell is a neuronal cell line. Neuronal cell lines are well known in the art, and include, but are not limited to, neuro-2A cells; B103; PC12; NT2; and the like. In some embodiments, the cell is a subject host cell.

The cell used in the screening method includes carboxyl-terminal truncated apoE in the cytosol. Carboxyl-truncated apoE can be produced by the cell, or can be provided exogenously.

In some embodiments, a nucleic acid that includes a nucleotide sequence that encodes apoE, as described above, is introduced into the cell, such that the carboxyl-terminal truncated apoE-encoding nucleic acid is transiently or stably expressed in the cell.

In other embodiments, a nucleic acid that includes a nucleotide sequence encoding full-length apoE is introduced into the cell, and the full-length apoE polypeptide that is produced undergoes proteolytic cleavage in the cell to yield carboxyl-terminal truncated apoE polypeptide in the cytosol.

In other embodiments, the cell is contacted with carboxyl-terminal truncated apoE polypeptide ("exogenous carboxyl-terminal truncated apoE polypeptide"). The cell takes up the exogenous carboxyl-terminal truncated apoE polypeptide from the medium. To facilitate uptake of exogenous carboxyl-terminal truncated apoE polypeptide, carboxyl-terminal truncated apoE polypeptide can be complexed with a compound that facilitates uptake into eukaryotic cells. Such compounds include, but are not limited to, very low density lipoprotein (VLDL), e.g., β-VLDL; phospholipid/apoE complex; cationic lipids; polyethylene glycol; polylactic-glycolic acid copolymer; dextran; and the like.

Whether the test agent has an effect on the formation of neurofibrillary tangles in the cell is determined using any known technique. For example, cells are stained with detectably-labeled antibodies specific for p-tau, p-NF-H, or apoE, to visualize intracellular inclusions of neurofibrillary tangles.

In some embodiments, cells are analyzed to determine whether the test agent has an effect on the level of carboxyl-terminal truncated apoE. Whether the test agent is effective in reducing the amount of carboxyl-terminal truncated apoE polypeptide in the cell is generally determined by analyzing cell lysates for the presence and/or amount of carboxyl-terminal truncated apoE.

In Vitro Cell-Free Assays

In other embodiments, a screening assay of the invention is an in vitro cell-free method. In vitro cell-free screening methods generally involve contacting an enzyme that mediates proteolytic cleavage of apoE with (1) a substrate for the enzyme, the substrate providing for a detectable signal when the enzyme is active; and (2) a test agent. A control sample includes the enzyme and the substrate, but no test agent.

The enzyme may be, but need not be, purified. The enzyme may be in a lysate of a cell that produces carboxyl-terminal truncated apoE; may be partially isolated; or may be substantially isolated (e.g., about 90%, about 95%, or about 98% pure.

Suitable substrates are those that provide a detectable signal when the substrate is acted on by the enzyme. A non-limiting example of such a substrate is a peptide of the formula $(P_3)_n P_2 P_1$-X, where $P_4 P_3 P_2 P_1$ is a peptide and X is a moiety (a "tag group") that is linked to the carboxyl terminus of the peptide, and that provides a detectable signal when cleaved from the peptide upon action by the enzyme; $P_1$ is a hydrophobic residue such as leucine, phenylalanine, or methionine; $P_2$ is proline; $P_3$ is a hydrophobic amino acid such as alanine; and $n \geq 2$. Non-limiting examples of suitable peptides include Ala-Ala-Pro-Phe (SEQ ID NO:1); Ala-Ala-Pro-Met (SEQ ID NO:2); Ala-Ala-Pro-Leu (SEQ ID NO:3); Ala-Ala-Ala-Ala-Pro-Phe (SEQ ID NO:4); and the like.

X is a tag group capable of being detected by assays that detect radiolabelled, photochemical, colorimetric, chromogenic, fluorescent, fluorogenic, phosphorescent, electrochemical, chemiluminescent or bioluminescent tags.

The compounds contain tags at the C-terminal position of the peptide. The tags are any known to those of skill in the art for use in enzyme assays. Tags include, but are not limited to, tags that are capable of being assayed, generally quantitatively, by radiolabels, by photochemical, colorimetric, chromogenic, fluorescent, fluorogenic, phosphorescent, electrochemical, chemiluminescent or bioluminescent or immunoassays. Exemplary tags are those detectable in colorimetric, chromogenic, fluorescent, fluorogenic, chemiluminescent or bioluminescent assays. Further exemplary tags are those the include a tag group that can be a radioactively tagged group, or a fluorogenic tag, a chromogenic tag or a chemiluminescent tag. All of these indicators form either an amide linkage or an ester linkage the $P_1$ amino acid such that these linkages are cleavable by the enzyme.

Chromogenic and fluorogenic labels and the use thereof are known in this art (see, e.g., U.S. Pat. Nos. 4,448,715; 3,884,896; 3,886,136; 4,016,042; 4,028,318; 4,119,620; 4,147,692; 4,155,916; 4,191,808; 4,191,809 4,207,232; and 4,167,449 which contain lists of specific chromogenic or fluorogenic substrates for various proteolytic enzymes; colorimetric substances are shown in U.S. Pat. Nos. 4,217,269, 4,210,497 and 4,221,706).

Fluorogenic or fluorescent tags suitable for use in the present methods include, but are not limited to, dansyl, 4-methylcoumaryl-7-amino, 4-trifluoromethylcoumaryl-7-amino, naphthylamino, 7-oxycoumaryl, 5-amino-iso-phthalic acid di(lower alkyl, preferably methyl or ethyl) ester, coumaryl-7-amino tagged with radioactive halogen or $^3$H, or naphthylamino tagged with radioactive halogen of $^3$H. Exemplary fluorogenic tags include 4-methylcoumaryl-7-amino or 4-trifluoromethylcoumaryl-7-amino. When the tag is a fluorogenic tag, it can be 4-methyl coumaryl-7-amino, 4-trifluoromethyl coumaryl-7-amino, naphthylamino, 7-oxycoumaryl, 5-amino isophthalic acid diethyl ester, dansyl, coumaryl-7-amino, 4-trifluoromethyl coumaryl-7-amino, 2-methylanthranilic acid.

Colorimetric or chromogenic tags suitable for use in the present methods include, but are not limited to, para-nitroanilino, para-nitrophenoxy, ortho-nitrophenoxy, ortho-carboxyphenoxy, nitrophenylamino, 1-carboxy-2-nitrophen-5-ylamino, 1-sulfo-2-nitrophen-5-ylamino, naphthylamino, μ-naphthylamino, β-naphthylamino, nitronaphthylamino, 5-nitro-α-naphthylamino, methoxynaphthylamino, 4-methoxy-μ-naphthylamino, quinonylamino, quinon-5-ylamino, nitroquinonylamino, 8-nitroquinon-5-ylamino, 4-methylcoumaryl-7-amino, 4-trifluoromethylcoumaryl-7-amino, and naphthylamino tagged with radioactive halogen.

When the tag is a chromogenic tag, it can be, for example, p-nitro-anilino, p-nitro-phenyloxy, nitrophenylamino, naphthylamino, nitronaphthylamino, methoxynaphthylamino, quinolylamino, nitroquinolylamino, 4-trifluoromethyl coumaryl-7-amino, or naphthylamino.

Chemiluminescent tags suitable for use in the present methods include, but are not limited to, luminol (5-amino-2,3-dihydro-1,4-phthalazinedione), iso-luminol (6-amino-2,3-dihydro-1,4-phthalazinedione) and N-(4-aminobutyl)-N-ethyl-iso-luminol (6-(N-(4-aminobutyl)-N-ethylamino)-2,3-dihyrophthalazine-1,4-dione). See, Simpson et al. (1979) Nature 279:646.

Radiolabelled tags suitable for use in the present methods include, but are not limited to, either $^{14}$C- or $^3$H-labelled anilino, benzylamino or lower alkoxy; or a halo label, in a hydroxyanilino, naphthylamino, hydroxybenzylamino or coumaryl-7-amino group.

Alternatively, the tag can be a reporter, such as chemiluminescent tag such as, amino-isoluminol, amino-luminol or other luminol derivative; or a bioluminescent tag, such as a luciferin, particularly a coelentrazine, or a luciferase, that upon cleavage is able to react with a suitable luciferase and luciferin, respectively. Also contemplated are immunoreporters, in which a reporter-labeled antibody (or antigen, i.e., ligand) binds to an antigen (receptor) on X; and biotin/avidin linked reporters.

In Vivo Screening Assays

In some embodiments, the assay methods involve contacting a transgenic, non-human animal of the invention with a test agent, and determining the effect, if any, of the agent on formation of neurofibrillary tangles, or any disorder associated with the presence of neurofibrillary tangles, in the animal.

In some embodiments, in vivo screening methods for identifying compounds that reduce the formation of carboxyl-terminal truncated apoE involve the use of transgenic non-human animals that include as a transgene a nucleic acid that encodes full-length apoE, and that produce, in neuronal cells, full-length apoE that is subsequently proteolytically processed to carboxyl-terminal truncated apoE. Transgenic, non-human animals that include as a transgene a nucleic acid that includes a nucleotide sequence encoding full-length apoE are known in the art. See, e.g., U.S. Pat. No. 6,046,381; Raber et al. (1998) Proc. Natl. Acad. Sci. USA. 95:10914-10919; Muttini (1999) J. Neurosci. 19:4867-4880.

In other embodiments, in vivo screening methods for identifying compounds that block the interaction of the carboxyl-terminal truncated apoE with p-tau and/or p-NF-H generally involve the use of subject transgenic non-human animals that include as a transgene a nucleic acid that encodes a carboxyl-terminal truncated form of apoE, and that produce, in neuronal cells, a carboxyl-terminal truncated apoE.

The methods generally involve contacting the transgenic, non-human animal with a test agent and determining the effect, if any, of a test agent on the level of carboxyl-terminal truncated apoE and/or the level of neurofibrillary tangles in a neuronal cell of the animal, compared to a control. A suitable control includes the transgenic animal not contacted with the test agent. Compounds identified using an in vivo screening assay of the invention are candidate compounds for treating disorders arising from the presence in a neuronal cell of C-terminal truncated forms of apoE, including AD.

The screen using the transgenic animals of the invention can employ any phenomena associated learning impairment, dementia or cognitive disorders that can be readily assessed in an animal model. The screening can include assessment of phenomena including, but not limited to: 1) analysis of molecular markers (e.g., levels of carboxyl-terminal truncated apoE protein in brain tissue; and formation of neurite plaques); 2) assessment behavioral symptoms associated with memory and learning; 3) detection of neurodegeneration characterized by progressive and irreversible deafferentation of the limbic system, association neocortex, and basal forebrain (neurodegeneration can be measured by, for example, detection of synaptophysin expression in brain tissue) (see, e.g., Games et al. *Nature* 373:523-7 (1995)). These phenomena may be assessed in the screening assays either singly or in any combination.

Generally, the screen will include control values (e.g., the level of neurofibrillary tangle formation in the test animal in the absence of test compound(s)). Test substances which are considered positive, i.e., likely to be beneficial in the treatment of apoE-mediated disorders, will be those which have a substantial effect upon formation of neurofibrillary tangles, and associated disorders (e.g., test agents that are able to rescue behavioral disorders caused by generation of carboxyl-terminal truncated apoE).

Methods for assessing these phenomena, and the effects expected of a candidate agent for treatment of apoE-associated disorders, are known in the art. For example, methods for using transgenic animals in various screening assays for, for example, testing compounds for an effect on AD, are found in WO 9640896, published Dec. 19, 1996; WO 9640895, published Dec. 19, 1996; WO 9511994, published May 4, 1995 (describing methods and compositions for in vivo monitoring of Aβ; each of which is incorporated herein by reference with respect to disclosure of methods and compositions for such screening assays and techniques). Examples of assessment of these phenomena are provided below, but are not meant to be limiting.

Pathological Studies

After exposure to the candidate agent, the animals are sacrificed and analyzed by immunohistology for either: 1) neurofibrillary tangles (NFTs) in the brain and/or 2) levels of carboxyl-terminal truncated apoE. The brain tissue is fixed (e.g, in 4% paraformladehyde) and sectioned; the sections are stained with antibodies reactive with carboxyl-terminal truncated apoE, and/or p-tau, and/or p-NF-H. Secondary antibodies conjugated with fluorescein, rhodamine, horse radish peroxidase, or alkaline phosphatase are used to detect the primary antibody. These experiments permit identification of neurofibrillary tangles and the regionalization of these NFTs to specific areas of the brain.

Sections can also be stained with other diagnostic antibodies recognizing antigens such as Alz-50, A2B5, Aβ, neuron-specific enolase, and others that are characteristic of neurodegeneration. Staining with thioflavins and congo red can also be carried out to analyze co-localization of Aβ deposits within the neuritic plaques and NFTs.

Analysis of Carboxyl-Terminal Truncated ApoE Production

Western Blot Analysis: Protein fractions can be isolated from tissue homogenates and cell lysates and subjected to Western blot analysis as described by Harlow et al., *Antibodies. A laboratory manual*, Cold Spring Harbor, N.Y., (1988); Brown et al., *J. Neurochem* 40:299-308 (1983); Tate-Ostroff et al., *Proc Natl Acad Sci* 86:745-749 (1989)); and Huang et al. (2001) *Proc. Natl. Acad. Sci. USA* 98:8838-8843. A brief description is given below.

The protein fractions can be denatured in Laemmli sample buffer and electrophoresed on sodium dodecyl sulfate (SDS)-polyacrylamide gels. The proteins are then transferred to nitrocellulose filters by electroblotting. The filters are blocked, incubated with primary antibodies, and finally reacted with enzyme conjugated secondary antibodies. Subsequent incubation with the appropriate substrate (which substrate provides for a detectable signal) reveals the position of carboxyl-terminal truncated apoE proteins.

Behavioral Studies

Behavioral tests designed to assess learning and memory deficits can be employed. An example of such as test is the Morris Water maze (Morris *Learn Motivat* 12:239-260 (1981)). In this procedure, the animal is placed in a circular pool filled with water, with an escape platform submerged just below the surface of the water. A visible marker is placed on the platform so that the animal can find it by navigating toward a proximal visual cue. Alternatively, a more complex form of the test in which there are no formal cues to mark the platform's location will be given to the animals. In this form, the animal must learn the platform's location relative to distal visual cues. Alternatively, or in addition, memory and learning deficits can be studied using a 3 runway panel for working memory impairment (attempts to pass through two incorrect panels of the three panel-gates at four choice points) (Ohno et al. *Pharmacol Biochem Behav* 57:257-261 (1997)).

Studies of Animal Models of Neuronal Damage

Rodent models of neuronal damage, for example neuronal damage caused by cerebral ischemia, may be examined to determine the role of apoE3 and apoE4 in the extent of neuronal damage caused by traumatic events as well as their role in neuronal remodeling, repair and recovery from such insults. Rodent models of cerebral ischemia, both global ischemia and focal ischemia, are useful for studying mechanisms controlling the occurrence of cerebral ischemia and potential therapeutic strategies for treatment of injury caused by ischemic events. Animal models of global ischemia, which is usually transient, have widely affected brain areas but typically give rise to neuronal alterations in selectively vulnerable brain regions. Examples of such models include, but are not limited to, the two vessel occlusion model of forebrain ischemia, the four vessel occlusion model of forebrain ischemia, and ischemia models involving elevated cerebrospinal fluid pressure. See Ginsberg and Busto, *Stroke*, 20:1627-1642 (1989), which is herein incorporated by reference. Models of focal ischemia may mimic ischemic stroke injury, and typically give rise to localized brain infarction. Examples of models of focal ischemia include, but are not limited to, middle cerebral artery occlusion, photochemically induced focal cerebral thrombosis, blood clot embolization, microsphere embolization and the like. See McAuley, *Cerebrovasc. Brain Metab. Review*, 7:153-180 (1995) which is herein incorporated by reference.

Methods of Inhibiting Formation of Neurofibrillary Tangles

The present invention provides methods for inhibiting formation of neurofibrillary tangles in a neuronal cell. The methods generally involve reducing the formation of carboxyl-terminal truncated form of apoE in a neuronal cell.

A reduction in the level of neurofibrillary tangles in a neuronal cell can be accomplished by: (1) reducing a level of carboxyl-terminal truncated apoE polypeptide; (2) reducing proteolytic cleavage of apoE polypeptide to a carboxyl-terminal truncated apoE polypeptide; (3) reducing interaction of a carboxyl-terminal truncated apoE polypeptide with p-tau; (4) reducing interaction of a carboxyl-terminal truncated apoE polypeptide with p-NF-H; (5) reducing a level and/or an proteolytic activity of an enzyme(s) that cleaves apoE to generate carboxyl-terminal truncated apoE.

In some embodiments, the methods involve introducing into an affected cell a peptide that includes at least amino acids 244-260 of apoE, and that inhibits the binding of carboxyl-terminal truncated apoE to p-tau and p-NF-H.

In other embodiments, the methods involve contacting a cell that produces carboxyl-terminal truncated apoE with an agent that inhibits the proteolytic activity of an enzyme(s) that cleaves apoE to generate carboxyl-terminal truncated apoE. In some embodiments, the agent is an inhibitor of chymotrypsin-like serine proteases. An agent that inhibits a chymotrypsin-like serine protease and that inhibits formation of carboxyl-terminal truncated apoE can be used in the methods of the invention.

Agents that are inhibitors of chymotrypsin-like serine proteases include those disclosed in U.S. Pat. Nos. 5,288,707; 6,127,340; and 6,281,206. Agents that inhibit a chymotrypsin-like serine protease include, but are not limited to, X-(aa$_4$)$_m$-(aa$_3$)$_n$-(aa$_2$)-(aa$_1$)-Z, wherein aa$_1$, aa$_2$, and aa$_3$ represent natural or unnatural acid residues and (aa$_4$)$_m$ one or more optional amino acid residues linked to the amino group of aa$_3$. Alternatively any one or more amino acids (aa) groups may be analogues of amino acid residues in which the α-hydrogen is replaced by a substituent. X represents H or a substituent on the N-terminal amino group, Z is —COOH or a C-terminal extension group (carboxy replacement group), for example as known in the art. In some compounds, Z is a heteroatom acid group, e.g. —B(OH)$_2$, —P(OH)$_2$ or PO(OH), or a derivative thereof, for example a carboxylic acid ester, a dioxo-boronate [—B(Osubstituent)$_2$] or a phosphate [—PO(Osubstituent)$_2$] or BF$_2$. Exemplary heteroatom analogue groups are —B(OH)$_2$ and —P(O)(OM)$_2$S(O)$_2$OH. In some embodiments, the P2-P1 natural peptide linkage is replaced by another linking moiety other than an N-substituted P2-P1 natural peptide linkage.

In some embodiments, an agent that inhibits formation of carboxyl-terminal truncated apoE is a peptide inhibitor. A non-limiting example of such an inhibitor is a peptide of the formula (P$_3$)$_n$P$_2$P$_1$, where P$_4$P$_3$P$_2$P$_1$ is a peptide; P$_1$ is a hydrophobic residue such as leucine, phenylalanine, or methionine; P$_2$ is proline; P$_3$ is a hydrophobic amino acid such as alanine; and n≧2. Non-limiting examples of suitable peptides include Ala-Ala-Pro-Phe (SEQ ID NO:1); Ala-Ala-Pro-Met (SEQ ID NO:2); Ala-Ala-Pro-Leu (SEQ ID NO:3); Ala-Ala-Ala-Ala-Pro-Phe (SEQ ID NO:4); and the like.

Therapeutic Agents

The invention provides agents identified using the methods described herein. Agents that reduce a level and/or an activity of carboxyl-terminal truncated apoE are used to treat apoE4-related disorders. An effective amount of the active agent is administered to the host, where "effective amount" means a dosage sufficient to produce a desired result. Generally, the desired result is at least a reduction in the level of carboxyl-terminal truncated apoE and/or a reduction in the level of neurofibrillary tangles in a neuronal cell as compared to a control. Generally, an agent identified by a screening method of the invention is formulated with one or more pharmaceutically acceptable excipients, as described in more detail below.

The invention provides therapeutic agents that reduces formation of carboxyl-terminal truncated apoE in a neuronal cell. Therapeutic agents include those that inhibit an enzyme that catalyzes the proteolytic degradation of apoE in neuronal cells (an "apoE cleavage enzyme") to produce carboxyl-terminal truncated apoE fragments; and agents that reduce activation of an apoE cleavage enzyme in neuronal cells with Aβ$_{1-42}$ and/or that inhibits an interaction between an apoE cleavage enzyme and Aβ$_{1-42}$. The therapeutic agents are specific, e.g., they inhibit an apoE cleavage enzyme that produces carboxyl-terminal truncated apoE fragments that induce formation of neurofibrillary tangles in neuronal cells, but not other enzymes in neuronal cells; and/or they reduce activation of an apoE cleavage enzyme in neuronal cells with Aβ$_{1-42}$, but do not substantially affect activation of other enzymes in neuronal cells; and/or they inhibit an interaction between an apoE cleavage enzyme and Aβ$_{1-42}$ in neuronal cells, but not other protein-protein interactions in neuronal cells. The therapeutic agents are useful in methods of the invention for treating a disorder associated with the presence in a neuronal cell of carboxyl-terminal truncated apoE.

In some embodiments, an agent that inhibits formation of carboxyl-terminal truncated apoE is a peptide inhibitor. A non-limiting example of such an inhibitor is a peptide of the formula (P$_3$)$_n$P$_2$P$_1$, where P$_4$P$_3$P$_2$P$_1$ is a peptide; P$_1$ is a hydrophobic residue such as leucine, phenylalanine, or methionine; P$_2$ is proline; P$_3$ is a hydrophobic amino acid such as alanine; and n≧2. Non-limiting examples of suitable peptides include Ala-Ala-Pro-Phe (SEQ ID NO:1); Ala-Ala-Pro-Met (SEQ ID NO:2); Ala-Ala-Pro-Leu (SEQ ID NO:3); Ala-Ala-Ala-Ala-Pro-Phe (SEQ ID NO:4); and the like.

In many embodiments, the agent is formulated with a pharmaceutically acceptable excipient. A variety of formulations are well known to those skilled in the art and are described in more detail below.

The invention provides a pharmaceutical preparation that includes: an inhibitor of a chymotrypsin-like protease inhibitor; an agent selected from the group consisting of an acetylcholinesterase inhibitor, a non-steroidal anti-inflammatory agent, a cyclooxygenase-2 inhibitor, and a monoamine oxidase inhibitor; and a pharmaceutically acceptable excipient.

In some embodiments, the invention provides compositions comprising an inhibitor of an enzyme that catalyzes the formation of carboxyl-terminal truncated apoE and at least one other therapeutic agent. Agents that inhibit an apoE cleavage enzyme are described above. Other therapeutic agents that can be formulated together with an inhibitor of an enzyme that catalyzes the formation of carboxyl-terminal truncated apoE include, but are not limited to, agents that are used to treat individuals with AD, including, but not limited to, acetylcholinesterase inhibitors, including, but not limited to, Aricept® (donepezil), Exelon® (rivastigmine), metrifonate, and tacrine (Cognex™); non-steroidal anti-inflammatory agents, including, but not limited to, ibuprofen and indomethacin; cyclooxygenase-2 (Cox2) inhibitors such as Celebrex; and monoamine oxidase inhibitors, such as Selegilene (Eldepryl or Deprenyl). Any known inhibitor of chymotrypsin-like serine proteases can be formulated together with another therapeutic agent used to treat AD. Dosages for each of the above agents are known in the art, and can be used in a pharmaceutical preparation with an apoE cleavage enzyme inhibitor. For example, Aricept® is generally administered at 50 mg orally per day for 6 weeks, and, if well tolerated by the individual, at 10 mg per day thereafter.

Pharmaceutically acceptable excipients are known to those skilled in the art, and have been amply described in a variety of publications, including, for example, A. Gennaro (1995) "Remington: The Science and Practice of Pharmacy", 19th edition, Lippincott, Williams, & Wilkins.

The invention further provides kits that include an agent that inhibits an apoE cleavage enzyme in a neuronal cell. The agent may be formulated with a pharmaceutically acceptable excipient. The kit may further include an additional agent for treating AD, as described above (e.g., an acetylcholinesterase inhibitor; a non-steroidal anti-inflammatory agent; a Cox-2 inhibitor; a monoamine oxidase inhibitor), which may also be formulated with a pharmaceutically acceptable excipient. The kit may further include a device for administering the formulation(s) to an individual. Devices include, but are not limited to, needles, syringes, catheters, and the like. The kit may further include information for use of the components of the kit, including information regarding dosing, administration, and the like. The information may be provided in any format, including, but not limited to, printed information.

Methods of Treating ApoE-Related Disorders

The present invention provides methods of treating apoE-related disorders (e.g., a disorder associated with the presence of carboxyl-terminal truncated apoE in a neuronal cell of the individual; e.g., AD) in an individual. The methods generally involve administering to an individual having an apoE-related disorder an effective amount of a compound that reduces formation of carboxyl-terminal truncated form of apoE in a neuronal cell in the individual and/or reduces formation of neurofibrillary tangles and/or reduces binding of carboxyl-terminal truncated apoE to p-tau and p-NF-H.

An "effective amount" of a compound is an amount that reduces a level of carboxyl-terminal truncated form of apoE in a neuronal cell in the individual and/or reduces a level of neurofibrillary tangles and/or reduces binding of carboxyl-terminal truncated apoE to p-tau and p-NF-H by at least about 10%, at least about 20%, at least about 30%, at least about 40%, at least about 50%, at least about 60%, at least about 70%, at least about 80% or more, compared to a level of carboxyl-terminal truncated form of apoE in a neuronal cell in the individual and/or a level of neurofibrillary tangles and/or binding of carboxyl-terminal truncated apoE to p-tau and p-NF-H in the absence of the compound.

In some embodiments, the invention provides a method of treating Alzheimer's disease. In some embodiments, the method involves assaying for the presence of carboxyl-terminal truncated apoE in a neuronal cell; and administering an inhibitor of an enzyme that catalyzes the formation of carboxyl-terminal truncated apoE in a neuronal cell. In other embodiments, the method involves administering an inhibitor of a chymotrypsin-like serine protease in an amount effective to inhibit an enzyme that catalyzes the formation of carboxyl-terminal truncated apoE in a neuronal cell, wherein the enzyme is inhibited and the level of neurofibrillary tangles in a neuronal cell in the individual is reduced.

The present invention further provides a method of treating an individual clinically diagnosed with a condition associated with the presence of carboxyl-terminal truncated apoE in a neuronal cell. The methods generally comprises analyzing a biological sample that includes a neuronal cell from an individual clinically diagnosed with an apoE-related disorder for the presence of carboxyl-terminal truncated apoE in a neuronal cell. The presence of carboxyl-terminal truncated apoE in a neuronal cell confirms the clinical diagnosis of a condition associated with apoE.

A treatment plan that is most effective for individuals clinically diagnosed as having a condition associated with apoE is then selected on the basis of the detected carboxyl-terminal truncated apoE in a neuronal cell. Treatment may include administering a composition that includes an agent that inhibits an apoE cleavage enzyme in a neuronal cell.

Information obtained as described above can be used to predict the response of the individual to a particular agent. Thus, the invention further provides a method for predicting a patient's likelihood to respond to a drug treatment for a condition associated with apoE, comprising determining whether carboxyl-terminal truncated apoE is present in a neuronal cell, wherein the presence of a carboxyl-terminal truncated apoE is predictive of the patient's likelihood to respond to a drug treatment for the condition.

Formulations, Dosages, and Routes of Administration

The invention provides formulations, including pharmaceutical formulations, comprising an agent that reduces a level and/or an activity of carboxyl-terminal truncated apoE. In general, a formulation comprises an effective amount of an agent that reduces a level and/or an activity of carboxyl-terminal truncated apoE. An "effective amount" means a dosage sufficient to produce a desired result, e.g., reduction in a level and/or an activity of carboxyl-terminal truncated apoE, a reduction in neurofibrillary tangles, an improvement in learning, memory, etc. Generally, the desired result is at least a reduction in a level and/or an activity of carboxyl-terminal truncated apoE as compared to a control. An agent that reduces a level and/or an activity of carboxyl-terminal truncated apoE may delivered in such a manner as to avoid the blood-brain barrier, as described in more detail below. An agent that reduces a level and/or an activity of carboxyl-terminal truncated apoE may be formulated and/or modified to enable the agent to cross the blood-brain barrier, as described in more detail below.

Formulations

In the subject methods, the active agent(s) may be administered to the host using any convenient means capable of resulting in the desired reduction in of a level and/or an activity of carboxyl-terminal truncated apoE, reduction in any apoE4-associated neurological disorder, reduction in an apoE4-associated activity, etc.

Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives-such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to be achieved, and the pharmacodynamics associated with each compound in the host.

Other modes of administration will also find use with the subject invention. For instance, an agent of the invention can be formulated in suppositories and, in some cases, aerosol and intranasal compositions. For suppositories, the vehicle composition will include traditional binders and carriers such as, polyalkylene glycols, or triglycerides. Such suppositories may be formed from mixtures containing the active ingredient in the range of about 0.5% to about 10% (w/w), preferably about 1% to about 2%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

An agent of the invention can be administered as injectables. Typically, injectable compositions are prepared as liquid solutions or suspensions; solid forms suitable for solution in, or suspension in, liquid vehicles prior to injection may also be prepared. The preparation may also be emulsified or the active ingredient encapsulated in liposome vehicles.

Suitable excipient vehicles are, for example, water, saline, dextrose, glycerol, ethanol, or the like, and combinations thereof. In addition, if desired, the vehicle may contain minor amounts of auxiliary substances such as wetting or emulsifying agents or pH buffering agents. Actual methods of preparing such dosage forms are known, or will be apparent, to those skilled in the art. See, e.g., Remington's Pharmaceutical Sciences, Mack Publishing Company, Easton, Pa., 17th edition, 1985; Remington: The Science and Practice of Pharmacy, A. R. Gennaro, (2000) Lippincott, Williams & Wilkins. The composition or formulation to be administered will, in any event, contain a quantity of the agent adequate to achieve the desired state in the subject being treated.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Dosages

Although the dosage used will vary depending on the clinical goals to be achieved, a suitable dosage range is one which provides up to about 1 μg to about 1,000 μg or about 10,000 μg of an agent that reduces formation of neurofibrillary tangles and/or reduces the level of carboxyl-terminal truncated apoE and/or reduces interaction of apoE with p-tau and p-NF-H can be administered in a single dose. Alternatively, a target dosage of an agent that reduces formation of neurofibrillary tangles and/or reduces the level of carboxyl-terminal truncated apoE and/or reduces interaction of apoE with p-tau and p-NF-H can be considered to be about in the range of about 0.1-1000 μM, about 0.5-500 μM, about 1-100 μM, or about 5-50 μM in a sample of host blood drawn within the first 24-48 hours after administration of the agent.

Those of skill will readily appreciate that dose levels can vary as a function of the specific compound, the severity of the symptoms and the susceptibility of the subject to side effects. Preferred dosages for a given compound are readily determinable by those of skill in the art by a variety of means.

Routes of Administration

An agent that reduces formation of neurofibrillary tangles and/or reduces the level of carboxyl-terminal truncated apoE and/or reduces interaction of apoE with p-tau and p-NF-H is administered to an individual using any available method and route suitable for drug delivery, including in vivo and ex vivo methods, as well as systemic and localized routes of administration.

Conventional and pharmaceutically acceptable routes of administration include intranasal, intramuscular, intratracheal, intratumoral, subcutaneous, intradermal, topical application, intravenous, rectal, nasal, oral and other parenteral routes of administration. Routes of administration may be combined, if desired, or adjusted depending upon the agent and/or the desired effect. The composition can be administered in a single dose or in multiple doses.

The agent can be administered to a host using any available conventional methods and routes suitable for delivery of conventional drugs, including systemic or localized routes. In general, routes of administration contemplated by the invention include, but are not necessarily limited to, enteral, parenteral, or inhalational routes.

Parenteral routes of administration other than inhalation administration include, but are not necessarily limited to, topical, transdermal, subcutaneous, intramuscular, intraorbital, intracapsular, intraspinal, intrasternal, and intravenous routes, i.e., any route of administration other than through the alimentary canal. Parenteral administration can be carried to effect systemic or local delivery of the agent. Where systemic delivery is desired, administration typically involves invasive or systemically absorbed topical or mucosal administration of pharmaceutical preparations.

The agent can also be delivered to the subject by enteral administration. Enteral routes of administration include, but are not necessarily limited to, oral and rectal (e.g., using a suppository) delivery.

Methods of administration of the agent through the skin or mucosa include, but are not necessarily limited to, topical application of a suitable pharmaceutical preparation, transdermal transmission, injection and epidermal administration. For transdermal transmission, absorption promoters or iontophoresis are suitable methods. Iontophoretic transmission may be accomplished using commercially available "patches" which deliver their product continuously via electric pulses through unbroken skin for periods of several days or more.

By treatment is meant at least an amelioration of the symptoms associated with the pathological condition afflicting the host, where amelioration is used in a broad sense to refer to at least a reduction in the magnitude of a parameter, e.g. symptom, associated with the pathological condition being treated, such as an apoE4-associated neurological disorder and pain associated therewith. As such, treatment also includes situations where the pathological condition, or at least symptoms associated therewith, are completely inhibited, e.g. prevented from happening, or stopped, e.g. terminated, such that the host no longer suffers from the pathological condition, or at least the symptoms that characterize the pathological condition.

A variety of hosts (wherein the term "host" is used interchangeably herein with the terms "subject" and "patient") are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, e.g. in oral or injectable doses, are provided. In such kits, in addition to the containers containing the unit doses will be an informational package insert describing the use and attendant benefits of the drugs in treating pathological condition of interest. Preferred compounds and unit doses are those described herein above.

Crossing the Blood-Brain Barrier

The blood-brain barrier limits the uptake of many therapeutic agents into the brain and spinal cord from the general circulation. Molecules which cross the blood-brain barrier use two main mechanisms: free diffusion; and facilitated transport. Because of the presence of the blood-brain barrier, attaining beneficial concentrations of a given therapeutic agent in the central nervous system (CNS) may require the use of drug delivery strategies. Delivery of therapeutic agents to the CNS can be achieved by several methods.

One method relies on neurosurgical techniques. In the case of gravely ill patients such as accident victims or those suffering from various forms of dementia, surgical intervention is warranted despite its attendant risks. For instance, therapeutic agents can be delivered by direct physical introduction into the CNS, such as intraventricular or intrathecal injection of drugs. Intraventricular injection may be facilitated by an intraventricular catheter, for example, attached to a reservoir, such as an Ommaya reservoir. Methods of introduction may also be provided by rechargeable or biodegradable devices. Another approach is the disruption of the blood-brain barrier by substances which increase the permeability of the blood-brain barrier. Examples include intra-arterial infusion of poorly diffusible agents such as mannitol, pharmaceuticals which increase cerebrovascular permeability such as etoposide, or vasoactive agents such as leukotrienes. Neuwelt and Rappoport (1984) *Fed. Proc.* 43:214-219; Baba et al. (1991) *J. Cereb. Blood Flow Metab.* 11:638-643; and Gennuso et al. (1993) *Cancer Invest.* 11:638-643.

Further, it may be desirable to administer the pharmaceutical agents locally to the area in need of treatment; this may be achieved by, for example, local infusion during surgery, by injection, by means of a catheter, or by means of an implant, said implant being of a porous, non-porous, or gelatinous material, including membranes, such as silastic membranes, or fibers.

Therapeutic compounds can also be delivered by using pharmacological techniques including chemical modification or screening for an analog which will cross the blood-brain barrier. The compound may be modified to increase the hydrophobicity of the molecule, decrease net charge or molecular weight of the molecule, or modify the molecule, so that it will resemble one normally transported across the blood-brain barrier. Levin (1980) *J. Med. Chem.* 23:682-684; Pardridge (1991) in: *Peptide Drug Delivery to the Brain*; and Kostis et al. (1994) *J. Clin. Pharmacol.* 34:989-996.

Encapsulation of the drug in a hydrophobic environment such as liposomes is also effective in delivering drugs to the CNS. For example WO 91/04014 describes a liposomal delivery system in which the drug is encapsulated within liposomes to which molecules have been added that are normally transported across the blood-brain barrier.

Another method of formulating the drug to pass through the blood-brain barrier is to encapsulate the drug in a cyclodextrin. Any suitable cyclodextrin which passes through the blood-brain barrier may be employed, including, but not limited to, J-cyclodextrin, K-cyclodextrin and derivatives thereof. See generally, U.S. Pat. Nos. 5,017,566, 5,002,935 and 4,983,586. Such compositions may also include a glycerol derivative as described by U.S. Pat. No. 5,153,179.

Delivery may also be obtained by conjugation of a therapeutic agent to a transportable agent to yield a new chimeric transportable therapeutic agent. For example, vasoactive intestinal peptide analog (VIPa) exerted its vasoactive effects only after conjugation to a monoclonal antibody (Mab) to the specific carrier molecule transferrin receptor, which facilitated the uptake of the VIPa-Mab conjugate through the blood-brain barrier. Pardridge (1991); and Bickel et al. (1993) *Proc. Natl. Acad Sci. USA* 90:2618-2622. Several other specific transport systems have been identified, these include, but are not limited to, those for transferring insulin, or insulin-like growth factors I and II. Other suitable, non-specific carriers include, but are not limited to, pyridinium, fatty acids, inositol, cholesterol, and glucose derivatives. Certain prodrugs have been described whereby, upon entering the central nervous system, the drug is cleaved from the carrier to release the active drug. U.S. Pat. No. 5,017,566.

Subjects Suitable for Treatment with a Therapeutic Agent of the Invention

A variety of subjects are suitable for treatment with an agent identified by a method of the invention. Suitable subjects include any individual, particularly a human, who has an apoE-associated disorder, who is at risk for developing an apoE-associated disorder, who has had an apoE-associated disorder and is at risk for recurrence of the apoE-associated disorder, or who is recovering from an apoE-associated disorder.

Such subjects include, but are not limited to, individuals who have been diagnosed as having Alzheimer's disease; individuals who have suffered one or more strokes; individuals who have suffered traumatic head injury; individuals who have high serum cholesterol levels; individuals who have A$\beta$ deposits in brain tissue; individuals who have had one or more cardiac events; subjects undergoing cardiac surgery; and subjects with multiple sclerosis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric.

Example 1

Characterization of Carboxyl-Terminal Truncated apoE in Neuronal Cells

Methods and Materials

Minimum essential medium (MEM), N2-medium supplements, and fetal bovine serum (FBS) were purchased from Life Technologies, Inc. Paraformaldehyde, streptolysin-O (STP-O), and Triton-100 were from Sigma (St. Louis, Mo.). The enhanced chemiluminescence (ECL) chemiluminescence detection kit for Western blots was from Amersham Life Science. Protein-A agarose was from Boehringer Mannheim. Recombinant human apoE3, apoE4, apoE3($\Delta$272-299), or apoE4($\Delta$272-299) were expressed in *E. coli* and purified using established techniques.

Polyclonal anti-human apoE antibody was from Calbiochem. Anti-apoE-carboxyl-terminal antibody (amino acids 272-299) was obtained by passing the polyclonal anit-apoE antibody for three times through a Sepharose CL-4B column that was coupled with a mixture of apoE3($\Delta$272-299) and apoE4($\Delta$272-299). The unbound fraction was used as anti-apoE-carboxyl-terminal antibody. Complete removal of antibodies against apoE-amino terminal portion (amino acids 1-271) was confirmed by western blotting on full-length apoE and apoE($\Delta$272-299).

Phosphorylation-dependent monoclonal anti-tau antibodies, AT8. (p-Ser202 and p-Thr205), AT100 (p-Ser212 and p-Thr214), AT180 (p-Thr231), AT270 (p-Thr181) were from Endogen. Phosphorylation-independent monoclonal anti-tau antibody, tau-1 (de-p-Ser202 and de-p-Thr205) and phosphorylation-dependent monoclonal anti-NF-H antibody, RT97, were from Boehringer Mannheim. Phosphorylation-dependent monoclonal anti-NF-H antibody, SM-31, was from Sternberger Monoclonals Inc. Monoclonal anti-NF-68, NR4, anti-NF-160, NN18, anti-NF-200 (NF-H), N52, and monoclonal anti-FLAG tag antibody, M2, were from Sigma. Fluorescein isothiocyanate (FITC)-, Rodamine-, or Cy5-coupled anti-rabbit or mouse IgG were from Vector. HRP-coupled anti-rabbit or mouse IgG was from Dako.

Preparation of apoE expression vectors—Polymerase chain reaction (PCR)-based molecular cloning techniques were used to construct various apoE expression vectors. PCR products encoding wild-type or modified forms of apoE3 or apoE4 were subcloned into a pFLAG-CMV-3 vector (Sigma), which has an N-terminal FLAG fusion peptide and a preprotrypsin signal sequence, thus, leading to secretion of the expressed proteins, or a p-FLAG-CMV-4 vector (Sigma), which has an N-terminal FLAG fusion peptide without a signal sequence, thus leading to expression of proteins in the cytosol. For some experiments, PCR products encoding wild-type or modified forms of apoE3 or apoE4 were subcloned into a pEGFP-C1 vector (Clontech), which has an amino-terminal green fluorescent protein (GFP) fusion without a signal sequence, thus, leading to expression of GFP-apoE fusion proteins in the cytosol. For all vectors, a human cytomegalovirus (CMV) immediate early promoter drives expression of the proteins. All DNA constructs used in this study and their properties were illustrated in Table I.

TABLE I

DNA constructs used in this study and their properties

| Constructs | Place of expression | N-terminal fusion |
|---|---|---|
| pFLAG-CMV-3 vector | | |
| ApoE3 | Secretory pathway | FLAG |
| ApoE4 | Secretory pathway | FLAG |
| ApoE3($\Delta$272-299) | Secretory pathway | FLAG |
| ApoE4($\Delta$272-299) | Secretory pathway | FLAG |
| ApoE4($\Delta$261-299) | Secretory pathway | FLAG |
| ApoE4($\Delta$252-299) | Secretory pathway | FLAG |
| ApoE4($\Delta$244-299) | Secretory pathway | FLAG |
| pFLAG-CMV-4 vector | | |
| ApoE3 | Cytosol | FLAG |
| ApoE3 | Cytosol | FLAG |
| ApoE3($\Delta$272-299) | Cytosol | FLAG |
| ApoE4($\Delta$272-299) | Cytosol | FLAG |
| ApoE4($\Delta$261-299) | Cytosol | FLAG |
| ApoE4($\Delta$252-299) | Cytosol | FLAG |
| ApoE4($\Delta$244-299) | Cytosol | FLAG |
| pEGFP-C1 vector | | |
| ApoE3 | Cytosol | GFP |
| ApoE3 | Cytosol | GFP |
| ApoE3($\Delta$272-299) | Cytosol | GFP |
| ApoE4($\Delta$272-299) | Cytosol | GFP |
| ApoE4($\Delta$261-299) | Cytosol | GFP |
| ApoE4($\Delta$252-299) | Cytosol | GFP |
| ApoE4($\Delta$244-299) | Cytosol | GFP |
| ApoE4($\Delta$1-232, $\Delta$272-299) | Cytosol | GFP |
| ApoE4($\Delta$1-20, $\Delta$272-299) | Cytosol | GFP |
| ApoE4($\Delta$1-45, $\Delta$272-299) | Cytosol | GFP |
| ApoE4($\Delta$1-84, $\Delta$272-299) | Cytosol | GFP |
| ApoE4($\Delta$1-126, $\Delta$272-299) | Cytosol | GFP |
| ApoE4($\Delta$1-170, $\Delta$272-299) | Cytosol | GFP |

Cell cultures—Murine neuroblastoma (Neuro-2a) cells were obtained from American Type Culture Collection (Rockville, Md.). Neuro-2a cells were maintained at 37° C. in a humidified 5% $CO_2$ incubator in MEM-containing 10% FBS, supplemented with non-essential amino acids, penicillin, and streptomycin.

Human teratocarcinoma cells (NT2) were maintained in Opti-MEM-I (GIBCO) containing 5% FBS and penicillin/streptomycin. The NT2 cells were differentiated into neuronal cells by retinoic acid treatment. Briefly, NT2 cells were incubated with 1 μM retinoic acid (RA) twice a week for 4 weeks. The cells were then replated in DMEM high glucose (DMEM/HG) containing 10% FBS and penicillin/streptomycin. One day later, the NT2 cells were replated on Matrigel-coated dishes (Collaborative Research). For the following 2 weeks, the differentiated NT2 (NT2-N) cells were maintained in DMEM/HG containing 10% FBS, penicillin/streptomycin, 1-β-D-arabinofuranosylcytosine (1 μM), fluorodeoxyuridine (10 μM), and uridine (10 μM). Thereafter, NT2-N cells were maintained in Opti-MEM-I containing 5% FBS and penicillin/streptomycin.

Primary cultures of cortical neurons were prepared from 17-day-old mouse embryos as previously described. Fiumelli et al. (1999) *Eur. J. Neurosci.* 11:1639-1646. Briefly, dissected cortexes were suspended in 2.5% trypsin solution for 15 minutes at 37° C., washed three times with calcium- and magnesium-free Hank's balanced salt solution, and then triturated with a glass pipette to dissociate the cells. Cells were then plated at a density of $2 \times 10^5/cm^2$ on poly-lysine treated dishes or chamber slides in DME medium supplemented with 1 mM glutamine, 7.5 mM sodium bicarbonate, 5 mM HEPES buffer (pH 7.0), 0.1 mg/ml streptomycin, and 0.06 mg/ml penicillin. A mixture of hormones and salt containing 25 µg/ml insulin, 100 µg/ml transferrin, 60 µM putrescine, 20 nM progesterone, and 30 nM sodium selenate was added into the culture medium. Cells were maintained for 6 days at 37° C. in a humidified atmosphere of 95% air and 5% $CO_2$. As reported previously (NS3307), immunostaining of 6 days in vitro cortical cultures with cell-specific antibodies yields >90% neuron-specific enolase-immunoreactive cells.

Transient transfection of cells—Neuro-2a, NT2-N, or cultured mouse primary neurons were transiently transfected with various apoE cDNA constructs, as listed in Table I, by using lipofectamine method. Briefly, 2 µg of apoE DNA were pre-incubated with 7 µl of lipofectamine in 200 µl of serum-free MEM containing N2-supplements at room temperature for 30 minutes. After addition of 800 µl of serum-free MEM containing N2-supplements, the mixture was added into the cells that had been washed three times with serum-free MEM. Ten to forty-eight hours later, the transfected cells were used for different experiments.

Immunocytochemistry—Neuro-2a cells were grown in 2-well chamber slides for 24 hours and were then transiently transfected with different apoE3 or apoE4 DNA constructs, as described above. After washing twice in PBS, the transfected cells were fixed with 3% paraformaldehyde in PBS for 30 minutes at room temperature, washed twice in PBS, and then permeabilized with Triton-X100 for 5 minutes which was followed by three washes in PBS.

To block nonspecific reactions, all slides were incubated for 1 hour at room temperature with PBS containing 2% BSA and 10% normal serum (Vector) derived from the same species as the source of secondary antibody (sheep or rabbit), followed by a 1-hour incubation with the primary antibody (monospecific rabbit anti-human apoE, 1:500; monoclonal anti-p-tau, 1:100-1:1000, anti-p-NF-H, 1:100-1:500) in PBS containing 2% BSA.

Slides were then washed three times in PBS containing 2% BSA and incubated for 1 hour at room temperature with the secondary antibody (FITC-coupled anti-rabbit IgG to detect antigen-bond anti-human apoE, Rodamine- or Cy5-coupled anti-mouse IgG to detect antigen-bond anti-p-tau or anti-p-NF-H). After three washes in PBS containing 2% BSA, immunofluorescently labeled slides were mounted in VectaShield (Vector) and viewed with a MRC-1024 laser scanning confocal system (Bio-Rad) mounted on an Optiphot-2 microscope (Nikon, Tokyo, Japan).

For double labeling (apoE and p-tau, p-NF-H, or FLAG tag), the FITC and Cy5 or Rodamine channels were viewed individually, and the resulting images were pseudocolored in green (FITC) or red (Cy5 or Rodamine) with Adobe Photo-Shop (version 5.5, Adobe System, San Jose, Calif.).

For the cells transiently transfected with GFP-apoE DNA constructs, after fixed in 3% paraformaldehyde and washed twice in PBS, the green fluorescence was viewed directly with a MRC-1024 laser scanning confocal system (Bio-Rad) as described above. In some experiments, transiently transfected Neuro-2a cells expressing GFP-apoE fragments were immunostained for p-tau and p-NF-H, as described above, to detect the co-localization of apoE fragments and p-tau and p-NF-H.

Differential permeabilization of cells with streptolysin-O and triton x-100—In some experiments, to determine whether the intracellular inclusions is in the cytosol or in subcellular organelles, Neuro-2a cells expressing apoE4 or apoE4(Δ272-299) were treated with seramin to remove cell surface-bond apoE, fixed with 3% paraformaldehyde, and then incubated with either 500 U/ml of streptolysin-O (STP-O) for 15 minutes at 4° C., which permeabilizes the plasma membranes of the cells without rupturing the subcellular organelle membranes, or 0.5% triton X-100, which permeabilizes both plasma and subcellular membranes. Then, anti-apoE immunostaining was performed as described above.

Immunoprecipitation and western blotting—Neuro-2a cells were grown to 80% confluence in 6-well plates or 15-cm dishes and were then transiently transfected with different apoE DNA constructs, as described above. Twenty-four to forty-eight hours later, the cells were harvested and lysed in ice-cold lysis buffer for 30 minutes. After spinning to remove nuclei (13,000 rpm for 15 minutes), apoE in supernatant was immunoprecipitated with monospecific rabbit anti-human apoE antibody and protein-A agarose beads. The immunoprecipitates were washed twice with lysis buffer and three times with PBS. The presence of apoE, p-tau, or p-NF-H in the immunoprecipitates was analyzed by western blotting using the corresponding antibodies. Alternatively, the supernatants of cell lysates were immunoprecipted with monoclonal anti-p-tau or anti-p-NF-H antibodies and, then, the presence of apoE was analyzed by anti-apoE western blotting.

For some experiments, brain tissues from normal individuals or Alzheimer's disease patients were homogenized in ice-cold lysis buffer I (50 mM Tris/HCl, pH 8.0, 150 mM NaCl, 0.1% SDS, 0.5% Nonidet P-40, 0.5% sodium deoxycholate, and a mixtures of protease inhibitors). After spin at 14,000 rpm for 30 minutes at 4° C. to get the solublized proteins (supernatant), the pellet was further homogenized in ice-cold lysis buffer II (50 mM Tris/HCl, pH 8.0, 150 mM NaCl, 4% SDS, 1% Nonidet P-40, 1% sodium deoxycholate, and a mixtures of protease inhibitors). Both supernatant and the solubilized pellet were subjected to SDS-PAGE and analyzed by western blotting as described above.

Electron microscopic analysis—Neuro-2a cells transiently transfected with DNA constructs encoding GFP or GFP-apoE4(Δ272-299) were lifted from the plates using 0.05% trypsin and 0.05 mM EDTA. The GFP positive cells were sorted with fluorescence-activated cell sorter (FACS) and pelleted by centrifugation. The cells were then fixed for 1 hour with 2.5% glutaraldehyde in 0.1M cacodylate buffer and post-fixed for 1 hour in 2% $OsO_4$. The cells were dehydrated, embedded in Epon 812, sectioned (80 nm) using a Reichert Ultracut E, and stained with uranyl acetate and lead citrate. The cells were then photographed using a JEOL CCX-100II electron microscope.

Results

Expression of ApoE4 Induces Formation of Intracellular Inclusions in Neuro-2a Cells.

To assess the role of apoE in NFT formation, the interaction of apoE3 or apoE4 with tau proteins in mouse neuroblastoma cells (Neuro-2a) transiently transfected with apoE3 or apoE4 cDNA constructs (Table I) was studied. Double-immunostaining of Neuro-2a cells expressing apoE4 with a polyclonal anti-apoE antibody and a monoclonal anti-p-tau antibody revealed both apoE and p-tau immunoreactive intracellular inclusions in a subset of transfected cells. These intracellular inclusions were also recognized by a monoclonal antibody against p-NF-H. Phosphorylation of tau or NF-H within the intracellular inclusions was confirmed by alkaline phosphatase treatment, which abolished anti-p-tau or anti-p-NF-H immunostaining. These results suggest the presence of a complex containing apoE, p-tau, and p-NF-H in a small number of apoE4-transfected cells. However, immunostaining of Neuro-2a cells expressing apoE3 did not reveal the formation of intracellular inclusions.

Amylpoid-Beta (Aβ) and Endoplasmic Reticulum (ER) Stress Increase the Formation of Intracellular Inclusions in Neuro2a Cells Expressing ApoE4.

Since Aβ deposition is a major pathological component within the brains of Alzheimer's disease patients, we determined the effect of Aβ treatment on the formation of apoE and p-tau immunoreactive intracellular inclusions in Neuro2a cells expressing apoE. The results are shown in FIG. 1. Aβ1-42 treatment clearly increased the number of inclusion-positive apoE4 expressing cells from 2.7±1.2% to 6.7±1.5% ($p<0.001$) and apoE3 expressing cells, from 0% to 2.8±0.6% ($p<0.001$). These results suggest that Aβ1-42 potentiates the formation of intracellular inclusions in Neuro2a cells expressing apoE.

Since Aβ treatment of cells can cause ER stress (TN98), other ER stress inducers, including Brefeldin A (BfA) and tunicamycin (TN98), were used to determine whether ER stress can increase the formation of intracellular inclusions in apoE transfected Neuro2a cells. Incubation with either BfA or tunicamycin increased the inclusion-positive cells from 2.7±1.2% to 7.2±2.1% ($p<0.001$) in apoE4 expressing cells and from 0% to 3.2±1.1% ($p<0.001$) in apoE3 expressing cells.

To test whether apoE directly interacts with p-tau and p-NF-H, coimmunoprecipitation studies were performed on cell lysates of apoE4-transfected Neuro-2a cells treated with Aβ1-42 or BfA. Immunoprecipitation using anti-p-tau revealed the presence of 2-3 bands (molecular weight 50-60 Kd) detected by anti-p-tau antibody on western blots. In addition, p-NF-H (molecular mass ~200 Kd) was also detected within the complex. However, anti-apoE western blotting did not reveal full-length apoE but rather a band with a lower molecular weight (~30 Kd instead of 34 Kd). These results confirm that the intracellular inclusions of the Neuro-2a cells are composed of p-tau and p-NF-H and demonstrate that the apoE4 in the complex is a truncated form with a molecular weight 10-15% smaller than the full-length apoE.

Carboxyl-Terminal Truncated ApoE induces Formation of Intracellular Inclusions in Neuro-2a Cells.

To determine whether the amino- or carboxyl-terminal truncation of apoE can induce formation of the intracellular inclusions, Neuro-2a cells were transfected with constructs possessing either amino- or carboxyl-terminal truncations of apoE. Deletion of up to 28 (~10%) amino-terminal amino acids of apoE4 did not result in formation of the intracellular inclusions. However, deletion of 28 (~10%) carboxyl-terminal amino acids from either apoE3 (Δ272-299) or apoE4 (Δ272-299) resulted in 32±5% or 78±8%, respectively, of the transfected cells displaying the intracellular filamentous inclusions. The intracellular inclusions in the Neuro-2a cells transfected with apoE4(Δ272-299) were immuno-reactive with anti-apoE, anti-p-tau, and anti-p-NF-H. There was complete merging of the immuno-reactivity of the inclusions, as shown for anti-apoE and anti-p-tau, indicating co-localization of apoE and p-tau). The intracellular inclusions induced by apoE3(Δ272-299) were similar but were smaller and were visible in many fewer cells. These results suggest that carboxyl-terminal truncated apoE, especially apoE4(Δ272-299), interacts with cytosolic p-tau and p-NF-H to induce the formation of intracellular inclusions in Neuro-2a cells.

More precise intracellular localization of the inclusions was ascertained by differential permeabilization of the apoE4 (Δ272-299) transfected Neuro-2a cells, followed by anti-apoE immunofluorescent staining. Streptolysin-O (STP-O) treatment, which permeabilizes the plasma membrane without permeabilizing subcellular organelle membranes, resulted in no significant anti-apoE immunoreactivity in apoE4 transfected Neuro-2a cells but strong anti-apoE immunoreactivity of the intracellular inclusions in apoE4(Δ272-299) transfected cells, suggesting the cytosolic distribution of the inclusions. However, Triton-X100 treatment, which permeabilizes both plasma and subcellular organelle membranes, resulted in strong anti-apoE immunoreactivity in both apoE4 and apoE4(Δ272-299) transfected cells. Taken together, these results indicate that the intracellular inclusions are cytosolic and suggest that apoE4(Δ272-299) synthesized in the endoplasmic reticulum (ER) escapes the secretory pathway and enters the cytosol, leading to interaction with cytosolic p-tau and p-NF-H. Alternatively, the secreted apoE4 (Δ272-299) is re-internalized and then escapes the endosomal-lysosomal pathway and enters the cytosol. Support of the first possibility comes from the observation that the apoE4 (Δ272-299) transfected cells secreted much less apoE into the medium than the apoE4 cells, even thought they had similar apoE mRNA levels.

Cytosolic ApoE(Δ272-299) Induces Formation of Intracellular Inclusions in Neuro-2a Cells.

We next tested whether direct expression of apoE(Δ272-299) in the cytosol of Neuro-2a cells would induce the formation of massive intracellular inclusions. Neuro-2a cells were transfected with GFP-apoE3(Δ272-299) or GFP-apoE4 (Δ272-299) DNA constructs lacking the sequence encoding the signal peptide. The green fluorescent protein (GFP) was fused to the N-terminus of the apoE to monitor the intracellular distribution. No apoE was secreted into the medium. After transient transfection of Neuro-2a cells, GFP alone was distributed very diffusely throughout the cells. Expression of GFP-apoE4(Δ272-299) in the cytosol, however, led to formation of massive intracellular filamentous inclusions in cell bodies, some of which extended into the neurites, whereas the GFP-apoE3(Δ272-299) had less ability to induce formation of intracellular inclusions in Neuro-2a cells than the GFP-apoE4(Δ272-299).

Figure 2:
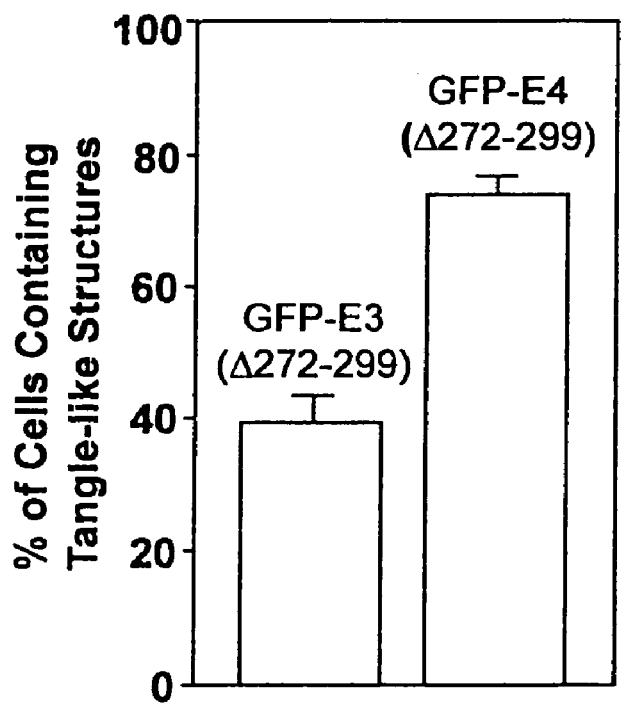
FIG. 2 is a graph depicting the percentage of GFP-apoE3 (Δ272-299)-transfected and GFP-apoE4(Δ272-299)-transfected cells that contain neurofibrillary tangles.

In contrast, the GFP-ApoE3 (full-length) was distributed in the cytoplasm around the nuclei and in the neurites, with a punctate or vesicular distribution pattern. On the other hand, the distribution of the GFP-apoE4 (full-length) was less punctate than GFP-apoE3. The percentage of cells containing neurofibrillary tangle-like inclusions was lower in GFP-apoE3(Δ272-299)-transfected cells, as compared to the GFP-apoE4(Δ272-299)-transfected cells, as shown in FIG. 2. These results suggest that the carboxyl-terminal 28 amino-acids of apoE protect apoE from interacting with p-tau and p-NF-H, thus preventing the formation of the intracellular inclusions.

Intracellular Inclusions Formed in Neuro-2a Cells Expressing ApoE4(Δ272-299) have Similar Ultrastructural and Biochemical Characteristics of Neurofibrillary Tangles Seen in Human Alzheimer's Disease Brains.

The ultrastructure and composition of the intracellular inclusions formed in Neuro-2a cells expressing cytosolic GFP-apoE4(Δ272-299) were determined. For ultrastructural analysis, electron microscopy revealed filamentous aggregates formed in the Neuro-2a cells expressing GFP-apoE4 (Δ272-299), but not in the cells expressing GFP alone. Filaments were randomly oriented, and were not membrane-bound. A high power magnification revealed that the inclusion is composed of many straight filaments, with a diameter of 10-20 nm, which are similar to some tangles seen in human Alzheimer's disease brains. The cells expressing GFP-apoE4(Δ272-299) also showed many electron dense membrane-bound organelles, suggestive of degenerating organelles.

To characterize the composition of the intracellular inclusions in more detail, two sets of monoclonal antibodies were used (Table II): anti-p-tau antibodies (AT8, AT100, AT180, AT270, and tau-2), which recognize phosphorylated serine or threonine residues at different positions in tau protein, and tau-1, which recognizes nonphosphorylated tau protein; anti-neurofilament antibodies, RT97 and N14, which recognize the phosphorylated NF-H, and N52, which recognizes nonphosphorylated NF-H.

TABLE II

Immunoreactivity of the NFT-like structures with various monoclonal antibodies against p-tau or p-NF-H

| Antibodies | Recognized residues in tau or NF-H* | Reactivity with NFT-like structures |
| --- | --- | --- |
| AT8 | p-Ser202, p-Thr205 | + |
| AT100 | p-Ser212, p-Thr214 | ++ |
| AT180 | p-Ser231 | − |
| AT270 | p-Thr181 | +++ |
| RT97 | KSP motif | +++ |
| SM31 | unknown | ++ |

*the residues or motif in human tau or NF-H.

It has been reported that the tangles in brains of Alzheimer's disease patients contain both p-tau and p-NF-H. Immunofluorescent staining of Neuro-2a cells expressing GFP-apoE4(Δ272-299) demonstrated that the inclusions were positive for some, but not all, of the monoclonal antibodies that recognize p-tau in paired helical filaments (PHF) in human Alzheimer's disease brains (Table II), suggesting that some, but not all, serine or threonine residues of tau protein were phosphorylated in the intracellular inclusions in Neuro-2a cells. Immunostaining with anti-p-NF-H antibody, RT97, demonstrated that the intracellular inclusion also contained p-NF-H.

To confirm the presence of both p-tau and p-NF-H, cell lysates containing the inclusions from apoE4(Δ272-299) transfected Neuro-2 cells were immunoprecipitated with anti-apoE antibody. Then, anti-p-tau antibody western blotting revealed proteins with molecular mass of 40-60 Kd, which were p-tau proteins. Likewise, anti-p-NF-H antibody (RT97) western blotting revealed p-NF-H with molecular mass of 200 Kd. Other bands with molecular mass of 40-60 Kd, characteristic of tau isoforms, were also recognized by monoclonal antibody RT97. It has been reported that monoclonal antibody RT97 cross-reacts with phosphorylated tau; therefore, these bands are likely p-tau proteins.

On the other hand, if the cellular lysates from apoE4(Δ272-299) transfected cells were immunoprecipted with monoclonal antibodies against p-tau or p-NF-H, anti-apoE western blotting revealed a band with molecular mass of ~30 KD, i.e., apoE4(Δ272-299). Taken together, these results suggest that apoE4(Δ272-299) forms a complex with p-tau and p-NF-H to form the intracellular inclusions in Neuro-2a cells. These intracellular inclusions have similar ultrastructural and biochemical characteristics of neurofibrillary tangles (NFT) seen in human Alzheimer's disease brains and, thus, we refer them to NFT-like structures.

Amino Acids 244-260 of ApoE Interact with p-tau and p-NF-H to Form the NFT-Like Structures in Neuro-2a Cells.

Figure 3A:
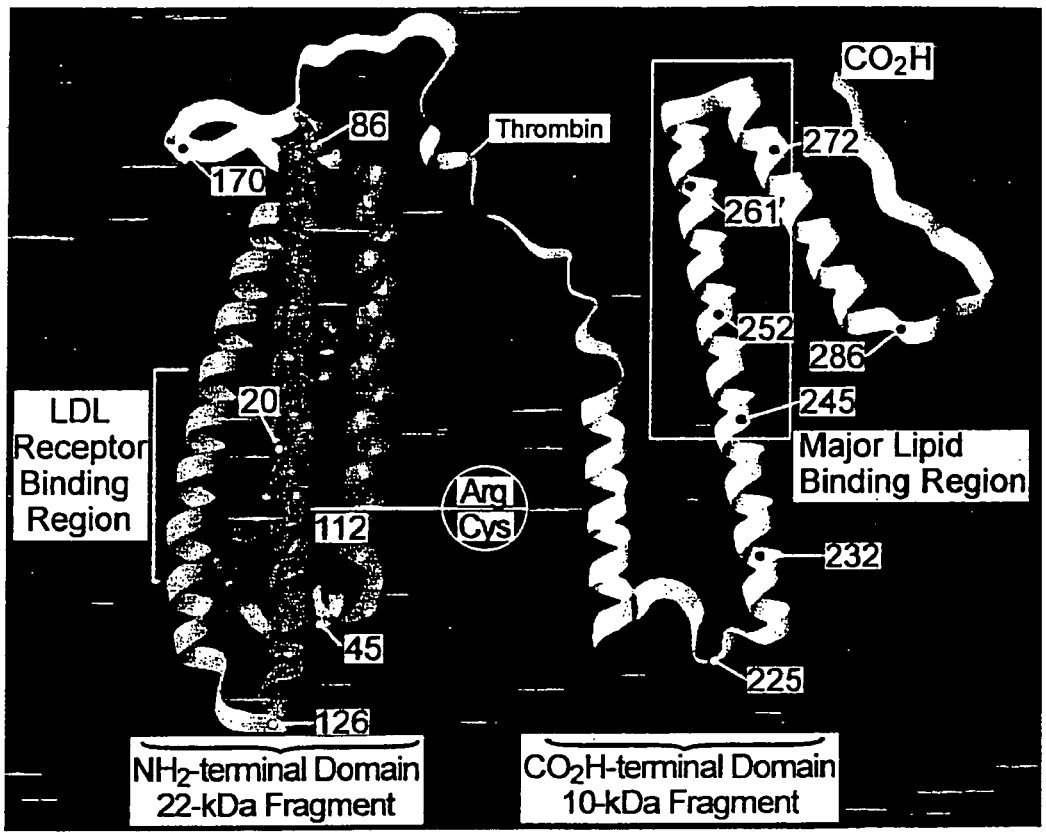
FIGS. 3A-C depict the structure of apoE (FIG. 3A); results indicating amino acids of apoE that interact with p-tau and p-NF-H (FIG. 3B); and results indicating the role of the amino terminal domain of apoE in formation of neurofibrillary tangles (FIG. 3C).
Figure 3B:
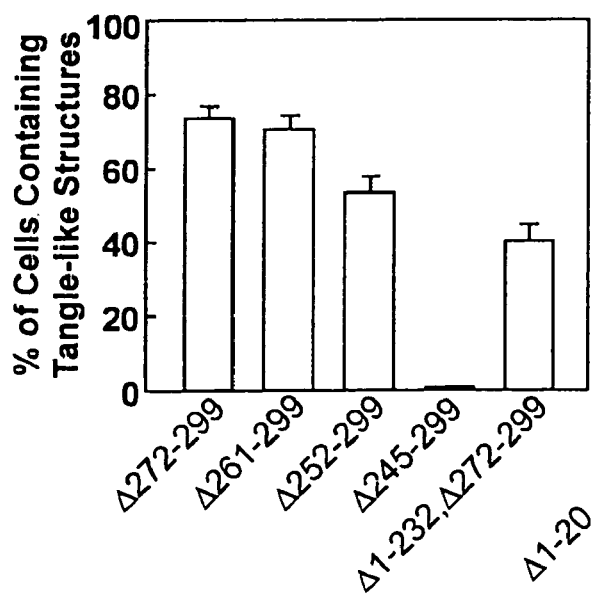

To determine the region of apoE that interacted directly with p-tau and p-NF-H to form the NFT-like structures, an additional series of carboxyl-terminal truncations on the GFP-apoE4(Δ272-299) DNA constructs (without signal peptide) were prepared and transfected into Neuro-2a cells. Sites of truncation are illustrated in FIG. 3A. The results are shown in FIG. 3B. Truncation to amino acid 260 (apoE4(Δ261-299)) did not alter the ability of the carboxyl-terminal truncated apoE4 to induce formation of the NFT-like structures, although truncation to amino acid 252 (apoE4(Δ252-299)) (slightly decreased the formation of the intracellular NFT-like structures. However, truncation to amino acid 244 (apoE4(Δ244-299)) abolished the formation of the NFT-like structures, suggesting that there are critical residues in the region 244-260 that are responsible for binding to p-tau and p-NF-H to form the NFT-like structures in Neuro-2a cells.

To confirm this observation, a GFP-apoE(Δ1-232, Δ272-299) DNA construct encoding only 38 amino acids of apoE (amino acids 233-271) (without signal peptide) was transfected into Neuro-2a cells. The results are shown in FIG. 3B. The apoE(Δ1-232, Δ272-299) induced formation of NFT-like structures in Neuro-2a cells, although these structures were much smaller and occurred in somewhat fewer transfected cells as compared with GFP-apoE4(Δ272-299) transfected cells. Thus, these results support the conclusion that the apoE amino acids 244-260 are required to induce formation of NFT-like structures in Neuro-2a cells and the amino-terminal domain of apoE influences the extent of NFT-like structure formation.

Amino-Terminal Domain of ApoE Modifies the Ability of the Carboxyl-Terminal Truncated ApoE to Form the NFT-Like Structures.

Figure 3C:
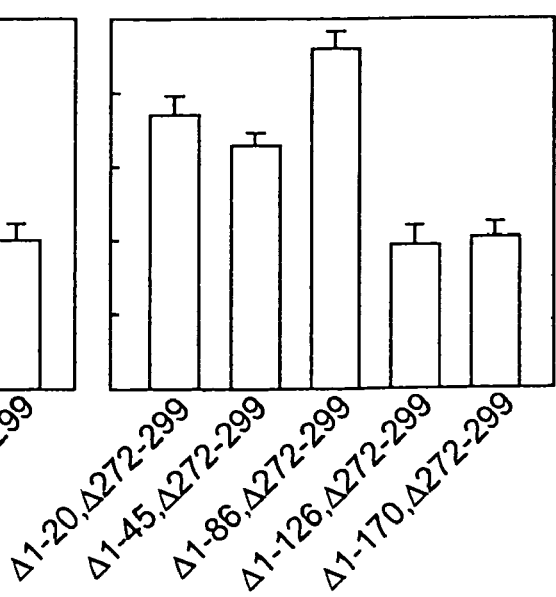

Since the sequence of amino acids 244-260 is identical in apoE3 and apoE4, this raises the question as to why apoE4(Δ272-299) has a greater ability than apoE3(Δ272-299) to form the NFT-like structures. To determine whether the amino-terminal domain of apoE can modify the ability of apoE amino acids 244-260 to induce formation of the NFT-like structures, a series of amino-terminal truncations on the GFP-apoE4(Δ272-299) DNA construct were made, as shown in FIG. 3A. The results are shown in FIG. 3C. Truncation of the first 20 amino acids (Δ1-20, Δ272-299), the first α-helix (Δ1-45, Δ272-299), and the second α-helix (Δ1-84, Δ272-299) did not alter the ability of GFP-apoE4(Δ272-299) to induce formation of the NFT-like structures in Neuro-2a cells. However, removal of the third α-helix (Δ1-126, Δ272-299) decreased dramatically the ability of the GFP-apoE4(Δ272-299) to induce formation of the NFT-like structures. Truncation of the fourth α-helix (Δ1-170, Δ272-299) did not decrease further the formation of the NFT-like structures. These results suggest that the sequence in the third α-helix (amino acids 85-126), which includes the position 112 where cysteine occurs in apoE3 and arginine in apoE4, modifies the ability of apoE4(Δ272-299) to induce formation of the NFT-like structures.

Formation of the NFT-Like Structures Induced by ApoE4 (4272-299) is Specific for Neurons.

To determine whether or not the formation of the NFT-like structures induced by apoE4(Δ272-299) is specific for neurons, we transfected two other neuronal cells, primary cultured embryonic mouse brain neurons and differentiated human teratocarcinoma NT2 cells (NT2-N), and four non-neuronal cell lines with GFP-apoE4(Δ272-299) (without signal peptide) (Table III).

TABLE III

Neuron-specific formation of NFT-like structures induced by GFP-apoE4(Δ272-299)

| Cell lines | Cell type | NFT-like structures |
|---|---|---|
| Neuronal cells | | |
| Neuro-2a | Neuron | + |
| NT2-N | Neuron | + |
| Mouse primary neurons | Neuron | + |
| Non-neuronal cells | | |
| CHO | Fibroblast | − |
| COS-7 | Fibroblast | − |
| C-6 | Astrocyte | − |
| HepG2 | Hepatocyte | − |
| McA-RH7777 | Hepatocyte | − |

NFT-like structures were determined by anti-apoE and anti-p-tau double-immunofluorescent staining as described in Experimental Procedures.

Expression of GFP-apoE4(Δ272-299) in the cytosol induced formation of the NFT-like structures in neuronal cells but not in non-neuronal cells, as shown in Table III, above. These results indicate that formation of the NFT-like structures induced by apoE4(Δ272-299) is specific for neurons, which is consistent with neuron-specific expression of tau and NF-H.

Internalized Exogenous ApoE4(Δ272-299) can Induce Formation of the NFT-Like Structures in Neuro-2a Cells.

In human brains, apoE is synthesized and secreted primarily by astrocytes, although human neurons are capable of producing apoE. The secreted apoE can be internalized by neurons. To determine whether internalized apoE4(Δ272-299) can induce formation of NFT-like structures in neurons. Neuro-2a cells were incubated with recombinant apoE4 (Δ272-299), which had been complexed with the lipid transport vehicle β-VLDL. After 30 hours incubation, neurite outgrowth and the formation of NFT-like structures in the cells were determined. Neuro-2a cells incubated with lipid transport vehicle alone for 30 hours showed neurite outgrowth. However, cells incubated with exogenous apoE4(Δ272-299) changed the morphology of the cells and did not show neurite outgrowth, suggesting that internalized apoE4(Δ272-299) might impair cytoskeletal structure and function. Anti-apoE immunofluorescent staining demonstrated that the NFT-like structures were formed in Neuro-2a cells incubated with exogenous apoE4(Δ272-299). These structures were identical to the tangle-like structures formed in Neuro-2a cells expressing GFP-apoE4(Δ272-299) in the cytosol. Therefore internalized apoE4(Δ272-299) can escape the endosomal-lysosomal pathway and interact with cytosolic p-tau and p-NF-H.

Carboxyl-Terminal Truncated ApoE can be Generated Inside Neurons.

To determine whether the carboxyl-terminal truncated forms of apoE generated naturally inside neurons, Neuro-2a cells were transfected with full-length apoE3 or apoE4 (with signal peptide), or Neuro-2a cells were incubated with exogenous full-length apoE3 or apoE4. After lysis of the cells, intracellular apoE was immunoprecipitated with a monospecific anti-apoE antibody. Anti-apoE western blotting revealed a full-length apoE band and a lower molecular weight band, the molecular mass of which was similar to apoE(Δ272-299) (~30 Kd). More fragments were generated from apoE4 than from apoE3. The lower molecular weight band represents a carboxyl-terminal truncated form of apoE, as detected by a monoclonal antibody, 6C5, which recognizes the amino-terminal 15 amino acids. Therefore, the shorter fragment is the carboxyl-terminal truncated form of apoE composed of approximately 270 amino acids. This conclusion was confirmed in transfected Neuro-2a cells expressing apoE4 with an amino-terminal FLAG tag. Anti-FLAG antibody also recognized a protein band with molecular mass of ~30 Kd.

Since Aβ1-42 increased formation of intracellular inclusions in Neuro2a cells expressing apoE4, we next determined whether treatment of the transfected cells with Aβ will increase generation of the carboxyl-terminal truncated form of apoE. Neuro-2a cells expressing apoE3 or apoE4 were incubated with Aβ1-42, then, intracellular apoE was immunoprecipitated and detected by anti-apoE western blotting. Treatment of the transfected cells with Aβ1-42 significantly increased the amounts of the carboxyl-terminal truncated forms of both apoE3 and apoE4, but more so with apoE4. Similar results were also obtained when exogenous apoE3 or apoE4 were incubated with Neuro-2a cells in the presence of Aβ1-42. These results suggest that Aβ1-42 may activate some unknown proteolytic enzymes that cleave apoE, especially apoE4, at its carboxyl-terminus, creating a biologically active truncated form.

Carboxyl-Terminal Truncated Forms of apoE are Found in Brains of Alzheimer's Disease Patients.

To determine whether carboxyl-terminal truncated forms of apoE can be generated in vivo in human brains, we analyzed apoE in brain lysates from normal or Alzheimer's disease patients by western blotting using polyclonal antibodies against full-length apoE or carboxyl-terminal portion of apoE (amino acids 272-299). The results are shown in FIGS. 4A-E.

Polyclonal anti-apoE revealed full-length apoE in both the supernatant and the pellet of brain lysates from normal and Alzheimer's disease patients. An apoE fragment with molecular mass of ~29 Kd was also recognized by polyclonal anti-apoE in supernatant from both normal and Alzheimer's disease brains, but to a greater extent in Alzheimer's disease brains. The 29-Kd apoE fragment was also found in the pellet of Alzheimer's disease brains, but not in the pellet of normal brains. In addition, smaller apoE fragments with molecular mass of ~14-19 Kd were found in both supernatant and the pellet of Alzheimer's disease brains but not of normal brains.

However, western blotting using antibody against carboxyl-terminal portion of apoE (amino acids 272-299) only revealed full-length apoE but not those apoE fragments in both supernatant and the pellets, suggesting that the fragments are carboxyl-terminal truncated forms of apoE. Also note that large complexes (molecular mass over 220 Kd) were detected in the pellets of Alzheimer's disease brains by anti-full-length apoE and anti-p-tau but not by anti-carboxyl-terminal apoE, suggesting that these large complexes contain carboxyl-terminal truncated forms of apoE and p-tau. Taken together, these results suggest that carboxyl-terminal truncated forms of apoE are generated to a much greater extent in Alzheimer's disease brains than in normal brains, and most of them are present in insoluble forms, probably forming complexes with p-tau.

Example 2

Analysis of Transgenic Mice Expressing apoE3 or apoE4 Specifically in CNS Neurons Generation of Transgenic Mice Transgenic mice expressing human apoE3 or apoE4 specifically in central nervous system (CNS) neurons were generated at the Gladstone Institutes as reported previously (Raber J. et al. Proc. Natl. Acad. Sci. USA. 1998, 95:10914-10919; Muttini M. et al. J. Neurosci. 1999, 19:4867-4880). The expression of apoE transgenes was driven by a neuron-specific enolase (NSE) promoter. NSE-apoE3 and NSE-apoE4 lines with matched cerebral levels of transgene expression were selected and crossed with Apoe$^{-/-}$ mice (C57BL/6J-Apoetm1Unc) from Jackson Laboratories (Bar Harbor, Me.). After elimination of wild-type mouse Apoe alleles in two generations of breedings among the resulting offspring, transgenic mice were further crossed with Apoe$^{-/-}$ mice to generate NSE-apoE3 and NSE-apoE4 mice that had at least 95% C57BL/6J genetic background. Crosses of NSE-apoE3 or NSE-apoE4 with C57BL/6J-Apoetm1Unc mice from Jackson Laboratories also yielded nontransgenic Apoe$^{-/-}$ littermates, which were used as controls.

Genotyping of Transgenic Mice

Mice transgenic for NSE-apoE3 or NSE-apoE4 were identified by Southern blot analysis of genomic tail DNA using a DNA probe for human APOE. NSE-apoE3 and NSE-apoE4 mice were differentiated by PCR. Because the human APOE intron 3 was included in the NSE-apoE4 but not in the NSE-apoE3 construct, the amplicon generated with intron 3-spanning primers (forward primer: nucleotides 3158-3175; reverse primer: nucleotides 3815-3834, GenBank accession number M10065) was 670 base pairs (bp) in NSE-apoE4 mice and 100 bp in NSE-apoE3 mice. Proteinase K-digested tail tissue (1:100 dilution, 2 μl) was subjected to touchdown PCR in a total reaction volume of 25 μl with each primer (0.2 μM), dNTPs (dATP, dCTP, dGTP, dTTP, 200 μM each), and 0.15 μl of AmpliTaq GoldR DNA polymerase (Perkin-Elmer, Norwalk, Conn.). The reaction was run on a GeneAmp PCR System 9600 thermocycler (Perkin-Elmer). Polymerase chain reaction (PCR) products were analyzed on 1.5% agarose gels.

Figure 5:
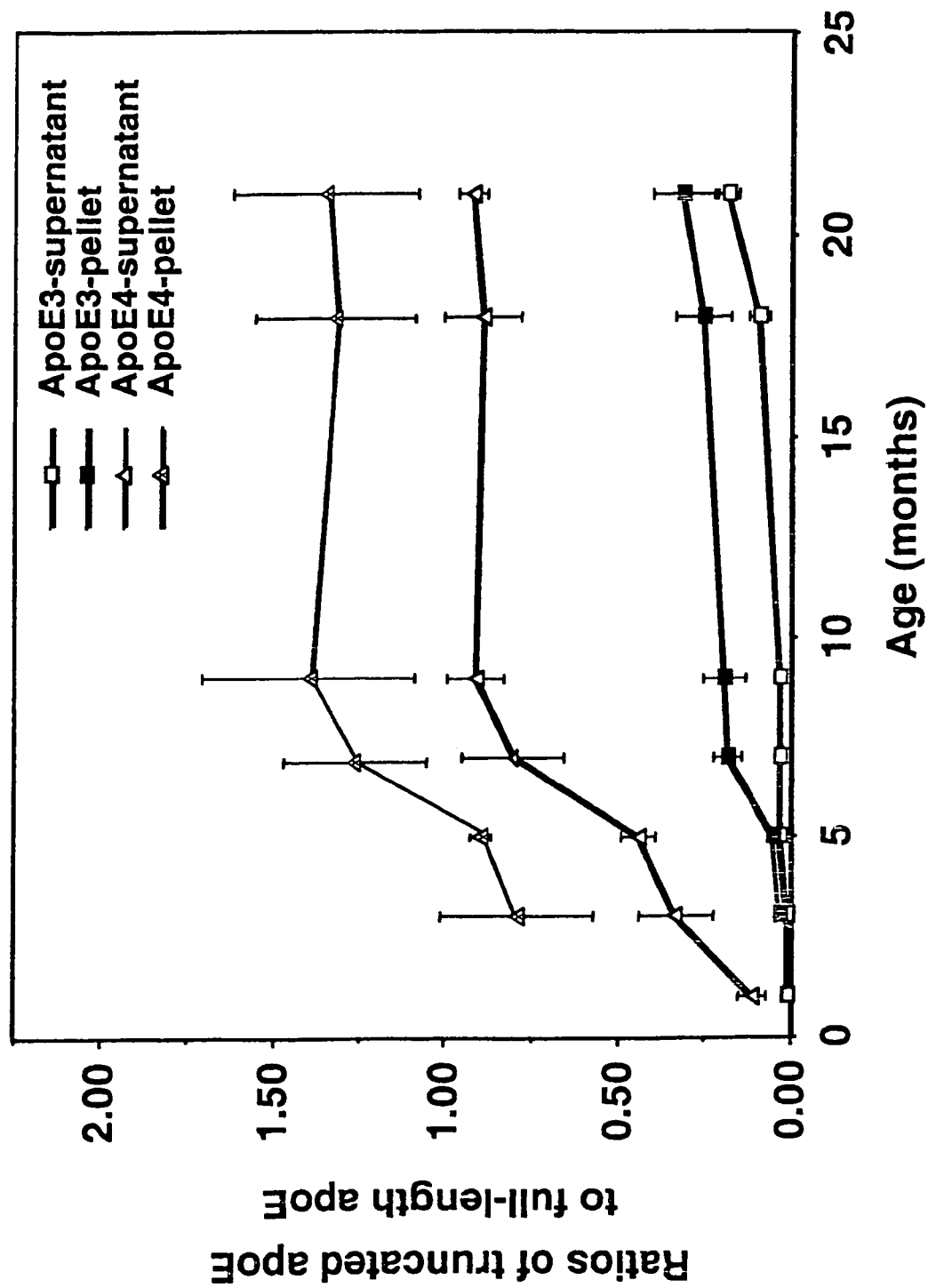
FIG. 5 is a graph depicting carboxyl-terminal truncated apoE3 and apoE4 in brains of NSE-apoE3 and NSE-apoE4 mice.

Age-Dependent Accumulation of C-Terminal Truncated Forms of ApoE4 in Brains of NSE-ApoE4 Transgenic Mice Since only female NSE-apoE4 mice displays neurodegenerative phenotypes after six months of age (Raber J. et al. Proc. Natl. Acad. Sci. USA. 1998, 95:10914-10919; Muttini M. et al. J. Neurosci. 1999, 19:4867-4880), we determined whether C-terminal truncated forms of apoE4 could be found in these mice. Anti-full-length apoE immunoblot revealed marked accumulation of the C-terminal truncated apoE fragments with molecular weight of 14-20 kDa in the brain lysate of a 7 month old NSE-apoE4 mouse, but not in the brain lysate of an age-matched NSE-apoE3 mouse. There was an age-dependent accumulation of the C-terminal truncated apoE4 fragments in both the supernatant and the solubilized pellet fractions of NSE-apoE4 mouse brains. As shown in FIG. 5, much less C-terminal truncated apoE3 fragments were found in the old NSE-apoE3 mouse brains. These results indicate that, like in human AD brains, the C-terminal truncated apoE4 fragments accumulated in brains of NSE-apoE4 mice with an age-dependent manner.

Age-Dependent Accumulation of p-Tau in Brains of NSE-ApoE4 Transgenic Mice

Figure 6:
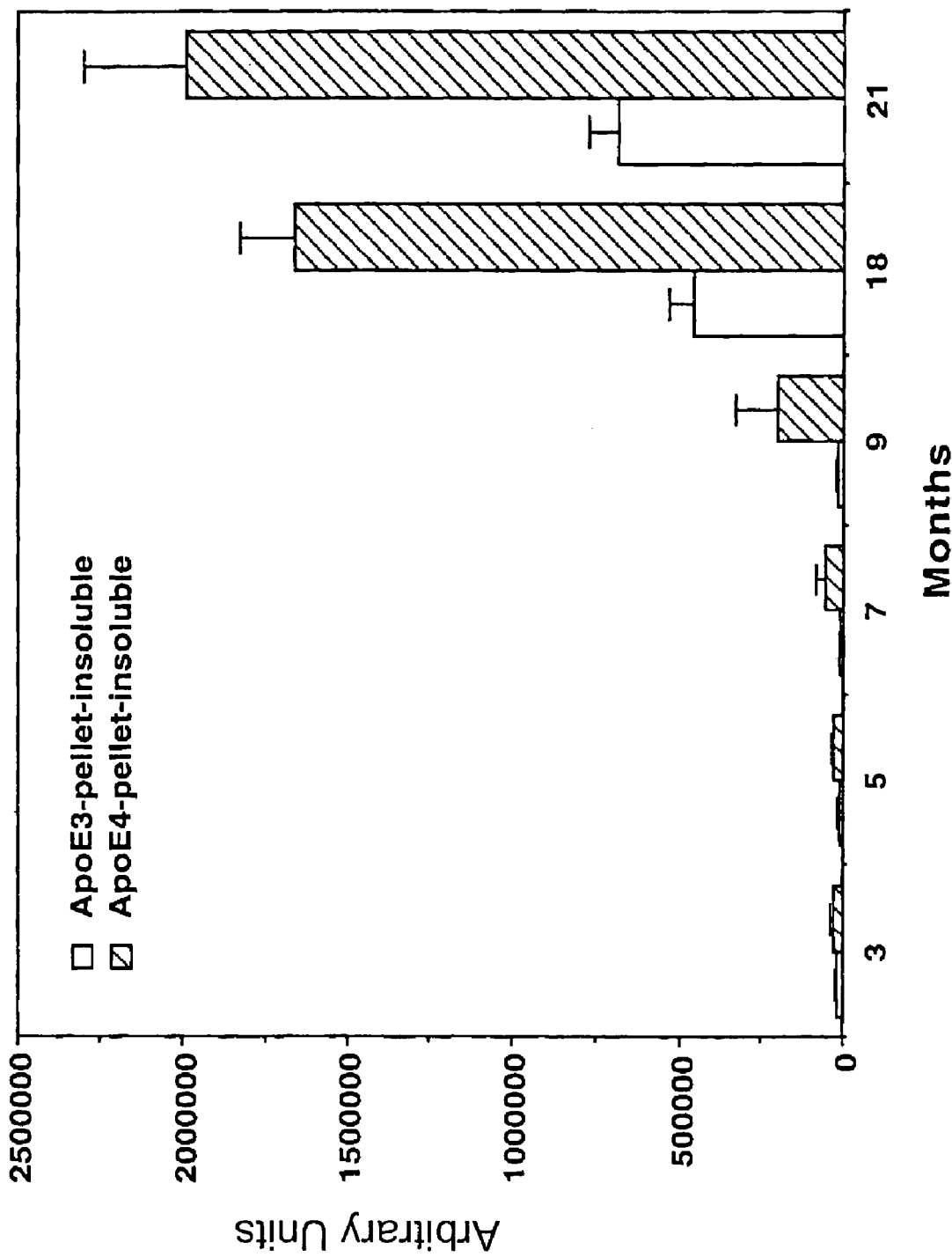
FIG. 6 is a graph depicting age-dependent accumulation of p-tau in brains of NSE-apoE mice.

Anti-p-tau (AT8) immunoblot revealed accumulation of the soluble p-tau (~50-60 kDa) in both supernatant and pellet fractions of brain lysates of NSE-apoE4 mice, but not of NSE-apoE3 mice, with ages up to 9 month old. The amount of the soluble p-tau (~50-60 kDa) decreased in the supernatant of brain lysates of NSE-apoE4 mice at the age of 18 months, whereas it increased in the supernatant of brain lysates of NSE-apoE4 mice with a similar age. However, as shown in FIG. 6, the insoluble p-tau (>200 kDa) dramatically accumulated in pellets of brain lysates of NSE-apoE4 mice at the age of 18 months. The insoluble p-tau (>200 kDa) was also increased in pellets of brain lysates of NSE-apoE3 mice at the age of 18 months, but to a much less degree as compared with the age-matched NSE-apoE4 mice. Thus, there was an age-dependent accumulation of both soluble and insoluble p-tau in brains of NSE-apoE4 transgenic mice, which is similar to those observed in human AD brains.

Figure 7:
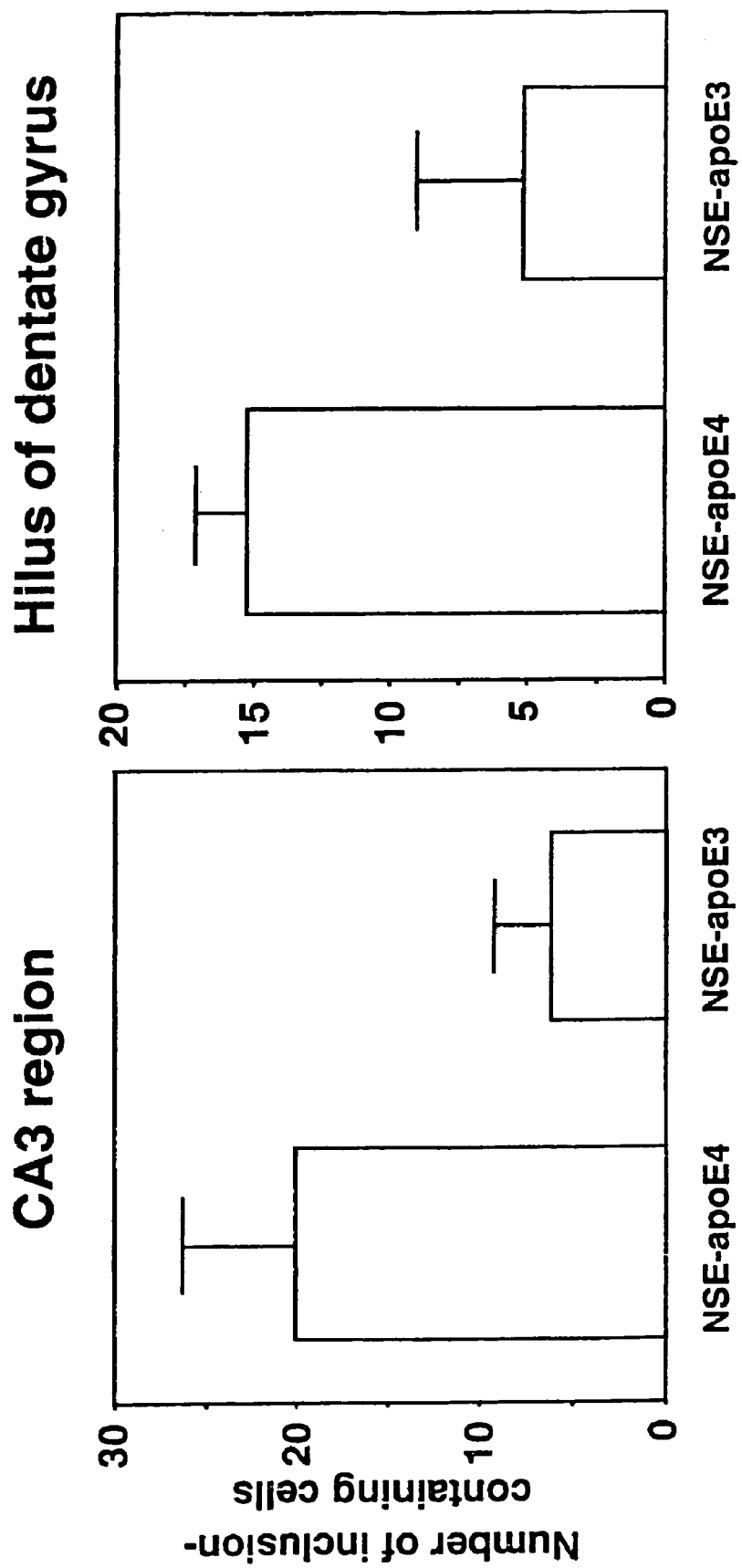
FIG. 7 is a graph depicting the occurrence of p-tau-positive intraneuronal inclusions in the hippocampus of NSE-apoE4 transgenic mice.

Occurrence of p-Tau (AT8) Positive Intraneuronal Inclusions in the Hippocampus of NSE-ApoE4 Transgenic Mice Immunostaining of brain sections with monoclonal antibody AT8, which recognizes the phosphorylated Ser202 and Ser205 residues of tau in NFTs, revealed intraneuronal inclusions in the CA3 region and the hilus of dentate gyrus in the hippocampus of NSE-apoE4 mice. These p-tau positive intraneuronal inclusions contained also apoE, which is the C-terminal truncated forms. As shown in FIG. 7, much less p-tau positive intraneuronal inclusions were found in the hippocampus of NSE-apoE3 mice. Therefore, the C-terminal truncated apoE may stimulate tau phosphorylation and induce p-tau positive intraneuronal inclusions in NSE-apoE4 transgenic mice.

Presence of an ApoE Cleavage Enzyme in Mouse Brain Lysates

Accumulation of the C-terminal truncated apoE4 in brains of NSE-apoE4 transgenic mice suggests the presence of apoE cleavage enzyme(s) in mouse brains, which preferentially cuts apoE4. To test this hypothesis, purified human apoE3 or apoE4 were incubated with brain lysates of apoE knockout mice at 37° C. for 3 hours and the proteolysis of apoE was analyzed by anti-apoE western blot. Anti-apoE revealed full-length apoE, apoE fragments of 28-30 kDa, and the fragments of 14-20 kDa, with much more fragments being generated from apoE4 than from apoE3. Anti-C-terminal apoE western blot indicated that these fragments were the C-terminal truncated forms of apoE. These results suggest that there is an enzyme(s) in mouse brain that cleaves apoE to generate C-terminal truncated fragments similar to those seen in human AD brains and in NSE-apoE4 transgenic mice. The results also suggest that apoE4 is much more susceptible to proteolytic cleavage.

Example 3

Characterization of an apoE Cleavage Enzyme

The apoE Cleavage Enzyme is a Serine Protease

To determine the biochemical properties of the putative apoE cleavage enzyme, we tested the effects of different known inhibitors for four major categories of proteases, i.e., serine proteases, cysteine proteases, aspartate proteases, and metalloproteases. Both EDTA and EGTA did not inhibit the cleavage of apoE4, suggesting that the enzyme is not a metalloprotease. Likewise, pepstain and Iodoacetimide or E-64 did not inhibit the cleavage of apoE4, indicating that the enzyme is not an aspartate protease nor a cysteine protease. PMSF totally abolished the cleavage activity, suggesting that the enzyme is a serine protease. Consistent with this conclusion, the complete inhibitor cocktail, which contains PMSF, also significantly inhibited the cleavage of apoE4.

The ApoE Cleavage Enzyme is a Chymotrypsin-Like Serine Protease.

Serine proteases can be categorized into the following groups: trypsin-like serine proteases, which cleave at the carboxyl side of basic residues (i.e., Arg or Lys), chymotrypsin-like serine proteases, which cleave at the carboxyl side of aromatic side chains (i.e., Phe or Trp) and of hydrophobic residues with larger side chain (i.e., Met), and elastase-like seine proteases, which cleave at the carboxyl side of hydrophobic residues (i.e., Ala or Val). To test the specificity of the apoE cleavage enzyme, we incubated many tri- or tetra-peptides with Arg/Lys, Phe, or Val/Ala at the C-terminal end, which are potential substrates for trypsin-like, chymotrypsin-like, and elastase-like seine proteases, respectively, with roughly purified apoE cleavage enzyme.

Figure 8:
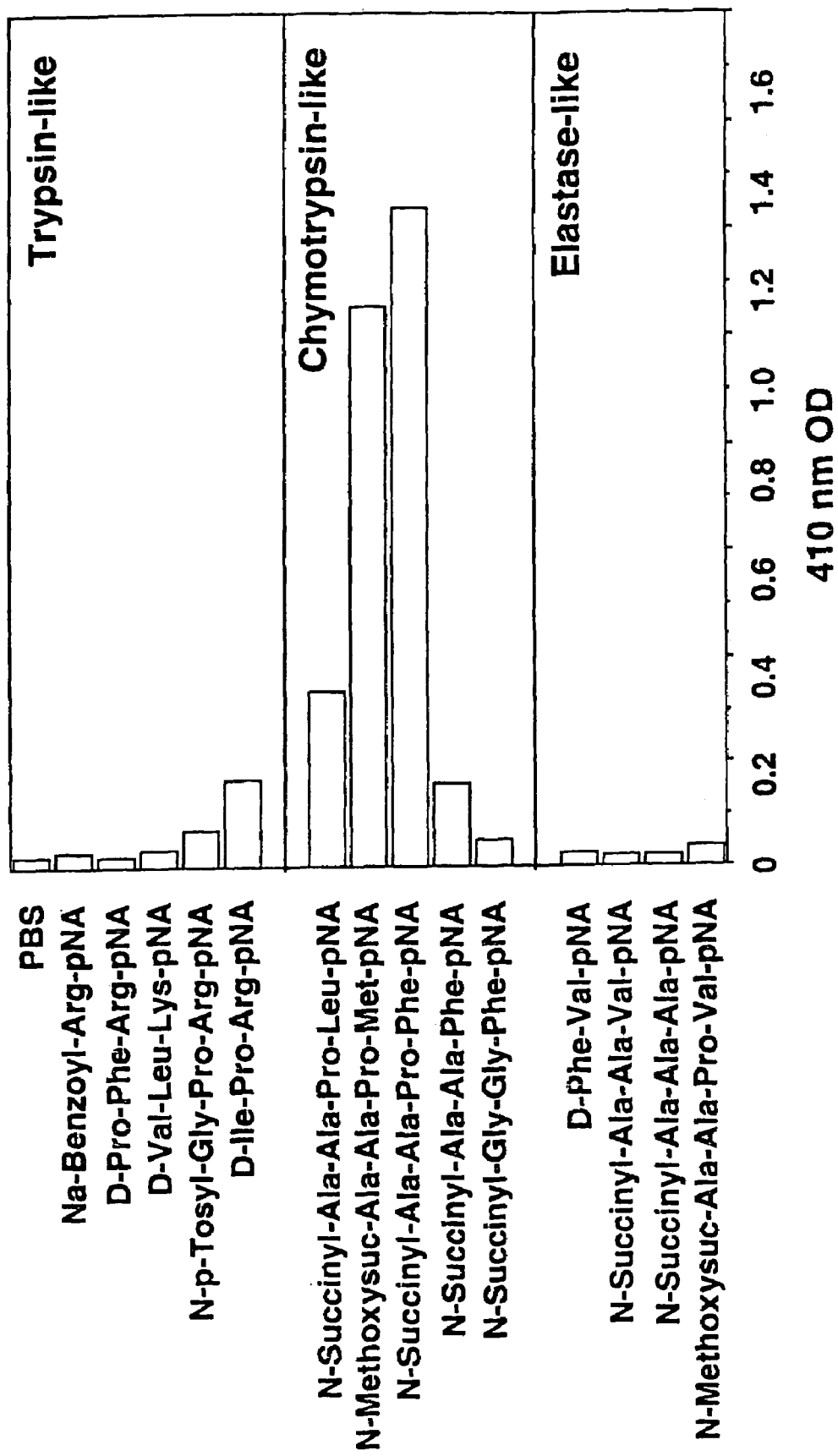
FIG. 8 is a graph depicting the effect of various agents on the enzymatic activity of an enzyme that catalyzes proteolytic cleavage of apoE.

To monitor the cleavage activity, a chromogenic group (p-nitroanilide) was added to the carboxyl-side of the last amino acid at the C-terminus. If the enzyme cuts the bond between the last amino acid and p-nitroanilide, the released p-nitroanilide will yield a yellow color, which can be monitored by a spectrophotometer at about 390-410 nm. FIG. 8 shows representative results obtained from these peptide substrates.

The results demonstrate that the putative apoE cleavage enzyme is a chymotrypsin-like serine protease, because it cuts at the carboxyl side of aromatic side chains (phenylalanine, Phe) and of hydrophobic residues with larger side chain (leucine, Leu; methionine, Met). Importantly, a proline at the P2 position and two hydrophobic amino acids (such as alanine, Ala) at the P3 and P4 positions are critical for determining the efficiency of the cleavage. Taken together, the putative apoE cleavage enzyme is a chymotrypsin-like serine protease, which recognizes the motif of Ala-Ala-Pro-Phe (SEQ ID NO:1), Ala-Ala-Pro-Met (SEQ ID NO:2), Ala-Ala-Pro-Leu (SEQ ID NO:3), or a similar sequence in the substrate peptides or proteins. By using Ala-Ala-Pro-Phe-p-nitroanilide as a substrate, the chromogenic assay can be used as a high-throughput method to screen drugs, agents, or chemical compounds that inhibit apoE cleavage activity. Para-nitroanilide is detected spectrophotometrically at about 390-410 nm.

Ala-Ala-Pro-Phe (SEQ ID NO:1), Ala-Ala-Ala-Ala-Pro-Phe (SEQ ID NO:4), and Ala-Ala-Pro-Leu (SEQ ID NO:3) are Peptide Inhibitors for the apoE Cleavage Enzyme.

Figure 9:
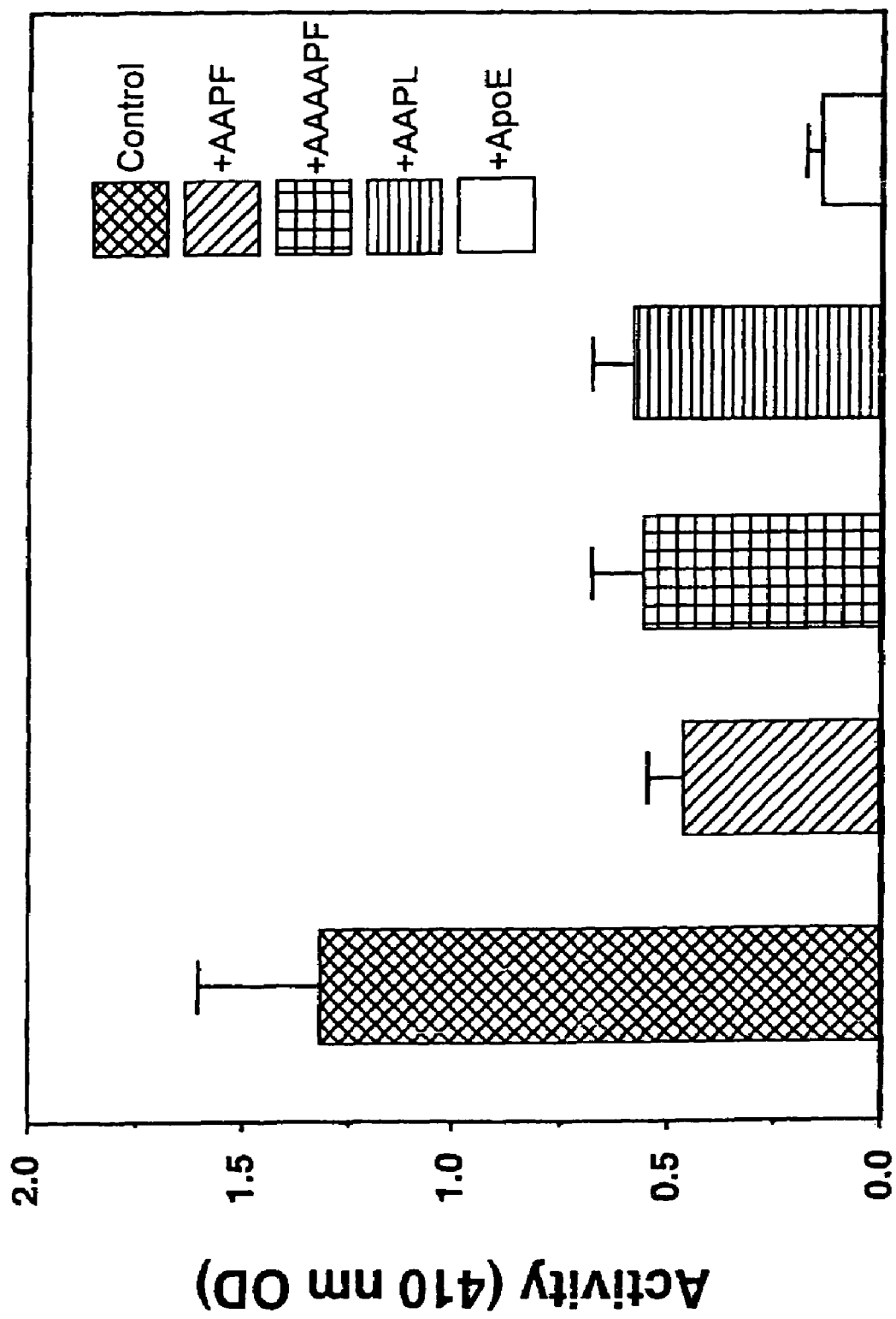
FIG. 9 is a graph depicting the results of inhibition of an apoE cleaving enzyme by various peptides.

By using the chromogenic assay, in which 1 mM Ala-Ala-Pro-Phe-p-nitroanilide was used as the substrate, we screened many peptides towards the inhibition of the apoE cleavage enzyme activity. As demonstrated in FIG. 9, 6 mM of peptides Ala-Ala-Pro-Phe (SEQ ID NO:1), Ala-Ala-Ala-Ala-Pro-Phe (SEQ ID NO:4), and Ala-Ala-Pro-Leu (SEQ ID NO:3) inhibited apoE cleavage enzyme activity by 67%, 58%, and 56%, respectively, at 20 hour incubation. Interestingly, 7 μM apoE4 inhibited the apoE cleavage enzyme activity by 89%.

The peptides Ala-Ala-Pro-Phe (SEQ ID NO:1) and Ala-Ala-Pro-Leu (SEQ ID NO:3) were further tested for the inhibition of apoE cleavage. After incubation of a peptide (1 mM) with 4 μg of apoE4 for 3 hours at 37° C. in the presence of the partially purified apoE cleavage enzyme, anti-apoE western blot revealed significant inhibition of apoE cleavage by both peptides. Thus, both Ala-Ala-Pro-Phe (SEQ ID NO:1) and Ala-Ala-Pro-Leu (SEQ ID NO:3) can be used as peptide inhibitors for the apoE cleavage enzyme.

It is evident from the above examples that the present invention provides carboxyl-terminal truncated apoE polypeptides; host cells that include carboxyl-terminal truncated apoE; methods of using transgenic animal models of carboxyl-terminal truncated apoE for identifying compounds that reduce formation of carboxyl-terminal truncated apoE; and compounds that inhibit the formation of apoE. Carboxyl-truncated apoE polypeptides are useful in generating host cells containing apoE for use in screening assays for compounds that inhibit the interaction of carboxyl-terminal truncated apoE with p-tau and p-NF-H. Compounds that inhibit the interaction of carboxyl-terminal truncated apoE with p-tau and p-NF-H, and compounds that reduce formation of carboxyl-terminal truncated apoE, reduce the formation of neurofibrillary tangles and are therefore useful in treating disorders associated with the formation of neurofibrillary tangles, including Alzheimer's disease, and related disorders.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of screening for biologically active agents that modulate a phenomenon associated with Alzheimer's disease (AD), the method comprising:
   (a) contacting a cell that produces a neurotoxic, hydrophobic, lipid-binding, carboxyl-terminal truncated apolipoprotein E (apoE) polypeptide with a test agent, wherein the neurotoxic carboxyl-terminal truncated apoE polypeptide comprises amino acids 244-260 of apoE; and
   (b) determining the effect of said agent on the level of the carboxyl-terminal apoE polypeptide in the cell, wherein an agent that reduces the level of the carboxyl-terminal truncated apoE polypeptide is a candidate agent for modulating a phenomenon associated with AD.

2. The method of claim 1, wherein the cell is a cell in a non-human transgenic animal that comprises, as a transgene, a nucleic acid that comprises a nucleotide sequence encoding apoE.

3. The method of claim 1, wherein the cell is an in vitro cell.

4. The method of claim 3, wherein the cell comprises a nucleic acid that comprises a nucleotide sequence that encodes the carboxyl-terminal truncated form of apoE.

5. The method of claim 1, wherein the apoE is apoE4.

6. The method of claim 5, wherein the carboxyl-terminal truncated form of apoE4 is apoE4(A272-299).

7. The method of claim 3, wherein the cell is a neuronal cell.

* * * * *

SEQUENCE LISTING

```
<160> NUMBER OF SEQ ID NOS: 4

<210> SEQ ID NO 1
<211> LENGTH: 4
<212> TYPE: PRT
<213> ORGANISM: Artificial Sequence
<220> FEATURE:
<223> OTHER INFORMATION: synthetic peptide

<400> SEQUENCE: 1

Ala Ala Pro Phe
 1

<210> SEQ ID NO 2
<211> LENGTH: 4
<212> TYPE: PRT
<213> ORGANISM: Artificial Sequence
<220> FEATURE:
<223> OTHER INFORMATION: synthetic peptide

<400> SEQUENCE: 2

Ala Ala Pro Met
```

```
<210> SEQ ID NO 3
<211> LENGTH: 4
<212> TYPE: PRT
<213> ORGANISM: Artificial Sequence
<220> FEATURE:
<223> OTHER INFORMATION: synthetic peptide

<400> SEQUENCE: 3

Ala Ala Pro Leu
 1

<210> SEQ ID NO 4
<211> LENGTH: 6
<212> TYPE: PRT
<213> ORGANISM: Artificial Sequence
<220> FEATURE:
<223> OTHER INFORMATION: synthetic peptide

<400> SEQUENCE: 4

Ala Ala Ala Ala Pro Phe
 1               5
```